US008550996B2

(12) United States Patent
Parshuram et al.

(10) Patent No.: US 8,550,996 B2
(45) Date of Patent: Oct. 8, 2013

(54) MEDICAL VITAL SIGN INDICATION TOOL, SYSTEM AND METHOD

(75) Inventors: Christopher Sushil Parshuram, Toronto (CA); Kristen Lynn Middaugh, Midland (CA)

(73) Assignee: The Hospital for Sick Children, Toronto (CA)

( * ) Notice: Subject to any disclaimer, the term of this patent is extended or adjusted under 35 U.S.C. 154(b) by 592 days.

(21) Appl. No.: 12/669,896

(22) PCT Filed: Jul. 25, 2008

(86) PCT No.: PCT/CA2008/001370
§ 371 (c)(1),
(2), (4) Date: Jun. 29, 2010

(87) PCT Pub. No.: WO2009/015466
PCT Pub. Date: Feb. 5, 2009

(65) Prior Publication Data
US 2010/0280333 A1 Nov. 4, 2010

Related U.S. Application Data

(60) Provisional application No. 60/952,447, filed on Jul. 27, 2007.

(51) Int. Cl.
*A61B 5/00* (2006.01)
(52) U.S. Cl.
USPC .............................. 600/301; 600/300; 705/43
(58) Field of Classification Search
USPC .................................. 600/300–301; 705/2–4
See application file for complete search history.

(56) References Cited

U.S. PATENT DOCUMENTS

| 5,365,425 | A | * | 11/1994 | Torma et al. ................... 705/2 |
| 5,839,438 | A | | 11/1998 | Graettinger et al. |
| 6,193,654 | B1 | | 2/2001 | Richardson et al. |
| 6,322,502 | B1 | | 11/2001 | Schoenberg et al. |
| 6,454,705 | B1 | | 9/2002 | Cosentino et al. |

(Continued)

FOREIGN PATENT DOCUMENTS

EP      0 764 914 A2      3/1997

OTHER PUBLICATIONS

An article entitled "The CRIB (Clinical Risk Index for Babies) Score: A Tool for Assessing Initial Neonatal Risk and Comparing Performance of Neonatal Intensive Care Units", *The Lancet*, 342:193-198 (1993).

(Continued)

*Primary Examiner* — Bill Thomson
*Assistant Examiner* — Bobby Soriano

(57) ABSTRACT

A vital sign evaluation tool (100, 200, 300) for evaluating a measure of severity of illness associated with a patient is provided, where the tool comprises a displayed grid (102) divided into a plurality of coded regions (104 to 106, 206, 306) each assigned to a vital sign associated with the patient. Each of the plurality of coded regions are scaled according to one of a plurality of age ranges (136, 202, 302) associated with the patient and adapted to generate a score value corresponding to a measurement of the vital sign. The score value within the plurality of coded regions is summed to produce a total score (156), where the total score is adapted to provide an indication of the severity of illness of the patient.

29 Claims, 19 Drawing Sheets

(56) References Cited

U.S. PATENT DOCUMENTS

| | | | |
|---|---|---|---|
| 7,097,617 B1 | 8/2006 | Smith | |
| 8,170,888 B2* | 5/2012 | Silverman | 705/3 |
| 2001/0012913 A1* | 8/2001 | Iliff | 600/300 |
| 2003/0139947 A1* | 7/2003 | Alemi et al. | 705/3 |
| 2005/0038332 A1* | 2/2005 | Saidara et al. | 600/347 |
| 2005/0060194 A1* | 3/2005 | Brown | 705/2 |
| 2005/0075535 A1 | 4/2005 | Shapiro et al. | |
| 2005/0102165 A1* | 5/2005 | Oshita et al. | 705/3 |
| 2005/0125256 A1 | 6/2005 | Schoenberg et al. | |
| 2005/0131739 A1* | 6/2005 | Rabinowitz et al. | 705/2 |
| 2005/0137484 A1* | 6/2005 | Griffin et al. | 600/509 |
| 2006/0085229 A9* | 4/2006 | Rosenfeld et al. | 705/2 |
| 2006/0189872 A1* | 8/2006 | Arnold | 600/483 |
| 2006/0206013 A1* | 9/2006 | Rothman et al. | 600/300 |
| 2006/0218007 A1* | 9/2006 | Bjorner et al. | 705/2 |
| 2006/0241972 A1 | 10/2006 | Lang et al. | |
| 2006/0265249 A1* | 11/2006 | Follis et al. | 705/3 |
| 2006/0271407 A1* | 11/2006 | Rosenfeld et al. | 705/3 |
| 2006/0287891 A1* | 12/2006 | Grasso et al. | 705/3 |
| 2006/0287906 A1* | 12/2006 | McGillin | 705/9 |
| 2007/0050206 A1* | 3/2007 | Whikehart et al. | 705/2 |
| 2007/0118399 A1* | 5/2007 | Avinash et al. | 705/2 |
| 2007/0162310 A1* | 7/2007 | Schmidt | 705/3 |
| 2007/0179347 A1* | 8/2007 | Tarassenko et al. | 600/300 |
| 2007/0185739 A1* | 8/2007 | Ober et al. | 705/3 |
| 2007/0198301 A1* | 8/2007 | Ayers et al. | 705/3 |
| 2007/0214013 A1* | 9/2007 | Silverman | 705/2 |
| 2007/0226007 A1* | 9/2007 | Osaki et al. | 705/2 |
| 2007/0239490 A1* | 10/2007 | Sullivan | 705/3 |
| 2008/0126124 A1* | 5/2008 | Schechter | 705/2 |
| 2008/0133141 A1* | 6/2008 | Frost | 702/19 |
| 2008/0162183 A1* | 7/2008 | Sachanandani et al. | 705/2 |
| 2008/0208623 A1* | 8/2008 | Fahey et al. | 705/2 |
| 2008/0214904 A1* | 9/2008 | Saeed et al. | 600/301 |
| 2008/0221927 A1* | 9/2008 | Levy | 705/3 |
| 2009/0231341 A1* | 9/2009 | Lord et al. | 345/440 |

OTHER PUBLICATIONS

Gorelick et al., "Revised Pediatric Emergency Assessment Tool (RePEAT): A Severity Index for Pediatric Emergency Care", *Academic Emergency Medicine*, 14:316-323 (2007).

Wiviott et al., "Performance of the Thrombolysis in Myocardial Infarction Risk Index in the National Registry of Myocardial Infarction-3 and -4", *Journal of the American College of Cardiology*, 44:783-789 (2004).

Kumar, N., et al., "Triage Score for Severity of Illness", Indian Pediatrics 40, 204-210 (2003).

Leteurtre, S., et al., "Validation of the paediatric logistic organ dysfunction (PELOD) score: prospective, observational, multicentre study", The Lancet 362, 192-197 (2003).

Shann, F., et al., "Paediatric index of mortality (PIM): a mortality prediction model for children in intensive care", Intensive Care Med. 23, 201-207 (1997).

* cited by examiner

| PEWS Score | | Recommendations | |
|---|---|---|---|
| Score | Response | Initial[1] | Subsequent[2] |
| 0 - 2 | Documentation<br>Charge Nurse Review<br>Paediatrician Review | 4 hours<br>routine<br>routine | routine<br>routine<br>routine |
| 3 - 4 | Documentation<br>Charge Nurse Review<br>Paediatrician Review | 2 -4 hours<br>< 8 hours<br>8 hours | 2 -4 hours<br>8 hourly<br>8 hourly |
| 5 - 6 | Documentation<br>Charge Nurse Review<br>Paediatrician Review<br>Continuous Monitoring<br>Additional Similar Patients | 1 -2 hours<br>< 4 hours<br>< 4 hours<br>consider<br>1RN: ≤ 2 | 1 - 2 hours<br>< 8 hourly<br>< 8 hourly<br>consider<br>1RN: ≤2 |
| 7 - 8 | Documentation<br>Charge Nurse Review<br>Paediatrician Review<br>Continuous Monitoring<br>ICU Consult<br>Additional Similar Patients | 15 - 60 min<br>< 2 hours<br>< 2 hours<br>consider<br>consider[3]<br>1RN: ≤ 1 | 30 - 60 min<br>< 4 hourly<br>< 4 hourly<br>consider<br>consider[3]<br>1RN: ≤1 |
| > 8 | Documentation<br>Charge Nurse Review<br>Paediatrician Review<br>Continuous Monitoring<br>ICU Consult<br>Additional Similar Patients | 15 - 30 min<br>< 15 min<br>< 15 min<br>continuous<br>consider[3]<br>none | 15 - 60 min<br>< 2 hourly<br>< 2 hourly<br>continuous<br>consider[3]<br>none |
| value<br><br>or<br><br>other | charting in 'value section" of<br>BPEWS record<br><br>or<br><br>other significant deterioration | immediate<br>consider<br>CPR<br>Monitoring<br>ICU consult | if patient stays on<br>ward formalize a<br>customized plan |

[1] Initial recommendations are intended to be applied when a patient either has their initial Bedside PEWS score calculated on admission to the hospital ward, or when the patients condition is changing when assessed by their recent Bedside PEWS scores.

[2] Subsequent recommendations are intended to assist level of care decision-making for children who after review have a BPEWS score remaining in the same category and who are cared for as a ward patient.

[3] ICU Consultation includes referral to a Medical Emergency Team or other "ICU Outreach" service. These items are recommendations to be applied at the discretion of the frontline health care professionals providing patient care. They are not intended to replace clinical judgement, but rather to augment it.

Fig. 6A

| Bedside PEWS Score | Initial Recommendation# | Response | Subsequent Recommendation^ |
|---|---|---|---|
| 0 – 2<br>'extremely' | 4 hours<br>Routine<br>Routine<br>2 or more | Documentation<br>Senior Ward Nurse Review<br>Physician Review Primary Team<br>Additional similar patients cared for by primary nurse | 4 hours<br>Routine<br>Routine<br>2 or more |
| 3 – 4<br>'very' | 2-4 hours<br>8 hours<br>8 hours<br>Routine<br>2 or more | Documentation<br>Senior Ward Nurse Review<br>Physician Review Primary Team<br>Senior Physician Review<br>Additional similar patients cared for by primary nurse | 2-4 hours<br>8 hours<br>8 hours<br>Routine<br>2 or more |
| 5 – 6<br>'somewhat' | 1-2 hours<br><4 hours<br><4 hours<br>Consider<br>1-2 | Documentation<br>Senior Ward Nurse Review<br>Physician Review Primary Team<br>Continuous Monitoring (Saturation)<br>Additional similar patients cared for by primary nurse | 1-2 hours<br><8 hourly<br><8 hourly<br>Consider<br>1-2 |
| 7 – 8<br>'not very' | 15-60 min<br><2 hours<br><2 hours<br><4 hours<br>Consider<br>Consider<br>Consider<br>0-1 | Documentation<br>Senior Ward Nurse Review<br>Physician Primary Team Review<br>Senior Physician Review<br>Continuous Monitoring (ECG, Saturation)<br>ICU consultation*<br>Additional similar patients cared for by primary nurse | 15-60 min<br><4 hourly<br><4 hourly<br>8 hourly<br>Consider<br>Consider<br>Reconsider<br>0-1 |
| >8<br>'not at all' | 15 min<br>< 15 min<br>< 15 min<br><15 min<br>Continuous<br>Consider<br>0 | Documentation<br>Senior Ward Nurse Review<br>Physician Review Primary Team<br>Senior Physician Review<br>Monitoring (ECG, Saturation)<br>ICU consultation*<br>Additional similar patients cared for by primary nurse | 15-60 min<br><2 hours<br><2 hours<br><4 hours<br>Continuous<br>Reconsider<br>0 |
| Any clinical sign in 'value' section of Bedside PEWS documentation record OR Other significant clinical deterioration | Immediate | Assess need for Cardiopulmonary Resuscitation<br>Call for immediate assistance<br>Continuous Monitoring (ECG, Saturation)<br>ICU consultation | Formalize a customized response and level of care plan for this particular child. |

Fig. 6B

MEDICAL VITAL SIGN INDICATION TOOL, SYSTEM AND METHOD

This application claims the benefit under 35 U.S.C. §119 (e) from U.S. Provisional Patent Application No. 60/952,447, filed on Jul. 27, 2007, the contents of which are incorporated by herein reference.

FIELD OF THE INVENTION

The present invention relates generally to a severity of illness indicator in patients, and in particular, to a system and method for developing a scoring system for preemptively identifying patients at risk of adverse events.

BACKGROUND OF THE INVENTION

Up to 3% of children admitted to hospital wards may require immediate medical assistance for treatment of adverse events such as actual or impending cardiopulmonary arrest. In both adults and children, preemptive management may prevent cardiopulmonary arrest and improve mortality, since the outcome of cardiopulmonary arrests in both adults and children is generally poor. Early identification and intervention may offer a means to prevent such adverse events (e.g., cardiopulmonary arrest) and thus improve patient outcomes. However, the provision of such preemptive care measures may rely on the timely identification of patients at risk and referral of these patients to the appropriate medical emergency team.

Two approaches to the timely identification of patients at risk may be used. First is the use of calling criteria, where patients meeting one or more specific triggering criteria are referred for medical treatment. Alternatively, "early warning" scores may be used. These "early warning" scores combine clinical parameters into a single score, such that patients with scores that exceed a predetermined threshold are identified and referred for medical treatment.

U.S. Pat. No. 7,097,617 to Smith describes a method of diagnosing patients having chronic pain, such as, medically unexplained symptoms or somatization, in order to assess a probability of relief of such pain through medical treatment. A self-reporting diagnostic test is provided that identifies and quantifies psychological and behavioral factors that can affect the treatment outcome for a patient sensitive to somatization. This might have a bearing on a decision by a physician to operate or otherwise medically treat a patient and the problems that could occur post-operatively or after treatment. The method diagnoses the probability of pain relief through medical treatment in a patient by administration of a test comprised of declarative statements of validity factors comprising defensiveness, predictiveness and carelessness, and clinical factors comprising somatic concern, depressed mode, passive personality, compulsive/obsessive personality, hypomania, and ego integrative defect. From the raw scores for each of the six (6) clinical factors, a scoring value of standard deviations above the normative group mean is calculated, enabling the clinician to produce a single numerical index score indicating and measuring the effect of somatization on the patient.

U.S. Pat. No. 6,454,705 to Cosentino et al. describes a medical system, apparatus, and method for monitoring and managing one or more ambulatory patients on a computer and allowing a caregiver to review the ambulatory patients' wellness parameters to provide treatment in accordance with the wellness parameters. The patient monitoring apparatus has a first communication device associated therewith for monitoring a patient's wellness parameters. A central computer is located remotely from the monitoring apparatus and in communication therewith. The central computer includes a second communication device for communicating wellness parameters and treatment data over a communications link established between the central computer and the patient monitoring apparatus, whereby the central computer is operated for querying the patient via the patient monitoring apparatus, receiving and processing measured wellness parameters from the patient monitoring apparatus, and calculating a score according to the wellness parameters. A main database is coupled to the central computer and includes patient medical records stored therein. One or more computer workstations are located remotely from and in communication with the central computer. The one or more computers have a third communication device for communicating physical examination data between the central computer and the one or more workstations over an established communication link. The score calculated by the central computer according to the wellness parameters is compared with a predetermined value, and based on the results of the comparison, the central computer issues an exception report. The exception report is communicated to the one or more remotely located workstations, whereby a caregiver located at the remote workstation site is notified of the exception report.

U.S. Pat. No. 6,322,502 to Schoenberg et al. describes a medical information system that receives patient data and information from various sources and displays such information in a variety of formats for use by members of a medical team in a hospital, clinic, or office. The medical information system includes a primary display, an associated display controller, and a system storage device. The controller is coupled to a primary interface unit. A keyboard and/or pointing device, a scanner, an audio input and/or output device, and a printer are all coupled by way of an interface to the display controller. Access to selected subsets of patient information is provided by user selection of specific data sets identified by job function selection icons. Multiple types of patient data are selectively displayed simultaneously, and to multiple remote users.

U.S. Pat. No. 5,839,438 to Graettinger et al. describes a neural network system and method for diagnosing patients', where medical conditions provide an efficient aid in identifying and interpreting factors which are significant in the medical diagnosis. The neural network system is trained to recognize medical conditions by being provided with input data that is available for a number of patients, and diagnosis is made by physicians in each case. Upon completion of the training period, the neural network system uses input measurement and interview data to produce a score, or a graded classification, of a patient's medical condition that is accompanied with a diagnosis interpretation. The diagnosis interpretation is a sorted catalogue of individual factors and interactions that influenced the score. The interpretive facility of the present invention is based on a comparison with a set of nominal values for each input factor or interaction. It can assist the physician in making a diagnosis of the patient's condition and can further provide a "second opinion" that may confirm the physician's findings, or point to ambiguities that call for a more detailed analysis.

U.S. Patent Application Publication No. 2006/0241972 to Lang et al. describes a method of measuring the effectiveness of a surgical or medical treatment carried out on a patient population. The method involves the steps of selecting a patient population, deriving pre-treatment score and post-treatment scores for each patient based on their questionnaire responses to quality of life-related criteria, deriving an adjusted score by subtracting the pre-treatment score from the post-treatment score, and analyzing the distribution of patients having each adjusted score to provide a measure of the effectiveness of the surgical or medical treatment. The population of patients may include patients having different values of a variable affecting the effectiveness of the surgical treatment. The effect of these variables on the adjusted scores may be analyzed by a computerized statistical software program.

U.S. Patent Application Publication No. 2005/0125256 to Schoenberg et al. describes a medical information system that receives patient data and information from various sources and displays such information in a variety of formats for use by members of a medical team in a hospital, clinic, or office. The medical information system receives patient information from doctors, pharmacists, patient monitoring equipment, testing laboratories, and/or computer databases. Access to selected subsets of patient information is provided by user selection of specific data sets identified by job function selection icons. A member of the medical team can record observations about a patient using key words and phrases which can be supplemented with additional text for customized notation. Multiple types of patient data are selectively displayed simultaneously, and to multiple remote users. The system can access stored data according to user-specified formulae to compute a score or metric which reflects a relationship between various factors, where each factor is weighted appropriately according to its significance, as defined in the formula. A user can selectively display data in graphic form by "clicking" on a row of tabular data in a tabular region of the display and "dragging and dropping" that row to a graphic display region of the display.

It is therefore at least one object of the present invention to provide a novel vital sign evaluation tool, system and method of preemptively identifying patients that are at risk of adverse events such as cardiopulmonary arrest.

SUMMARY OF THE INVENTION

According to one aspect there is provided a vital sign evaluation tool for evaluating a measure of severity of illness associated with a patient, the tool comprising a displayed grid divided into a plurality of coded regions each assigned to a vital sign associated with the patient, each of the plurality of coded regions scaled according to one of a plurality of age ranges associated with the patient and adapted to generate a score value corresponding to a measurement of the vital sign, the score value within the plurality of the coded regions summed to produce a total score, wherein the total score is adapted to provide an indication of the severity of illness of the patient and is mapped to an associated care recommendation.

According to one embodiment, the displayed grid comprises a chronological axis that is adapted to facilitate entering the score value at one or more times during a time period, whereby the score value comprises an integer value that increases based on the vital sign deviating from normality. The total score may comprise an integer value that increases based on an increase in the severity of illness.

According to another embodiment, the vital sign is one of a measure of respiratory rate, a measure of heart rate, a measure of respiratory effort, a measure of oxygen therapy, a measure of capillary refill time, a measure of transcutaneous oxygen saturation, and a measure of systolic blood pressure.

According to yet another embodiment, the plurality of coded regions each comprise a plurality of color-coded sections, where the score value is generated based on mapping a color associated with each one of the plurality of color coded sections with the integer value associated with the score value. Each one of the plurality of color-coded sections comprises at least one color-coded row.

According to still yet another embodiment, the displayed grid comprises a physical medium upon which the score and total score is entered, where the grid includes an interactive display associated with an electronic device into which the score and total score is entered, or a chart such as a paper sheet into which the score and total score is entered.

According to another aspect there is provided a method of evaluating a measure of severity of illness in a patient, where the method comprises providing an age range associated with the patient; assigning a plurality of coded regions (e.g., a plurality of assigned colors) to measurements associated with each of a plurality of vital signs based on the provided age range; measuring the plurality of vital signs associated with the patient; associating one of the plurality of coded regions to each of the measured vital signs; assigning a score value to each of the associated plurality of coded regions; determining a total score from the score value assigned to each of the associated plurality of coded regions; determining a measure of the severity of illness based on the total score; and determining a care recommendation based on said measure.

According to one embodiment, the method may further comprise admitting the patient to an intensive care unit (ICU) based on the total score exceeding a pre-determined threshold.

According to another embodiment, the method may further comprise assigning medical staffing needs based on the total score calculated for a plurality of patients, where assigning the medical staffing needs includes, for example, assigning a pre-defined number of nurses to the plurality of patients based on the total score calculated for the plurality of patients.

According to yet another embodiment, the method may further include determining the total score at multiple times during a 24-hour period and/or detecting a measure of the severity of illness based on changes in the determined total score at multiple times. Determining the total score at multiple times during a 24-hour period may include determining the total score at set-time intervals during a 24-hour period.

According to yet another embodiment, the method may further comprise evaluating a variation in score value for a selected one of the measured plurality of vital signs by observing the variation in score value at set time intervals, whereby the variation in score value may be evaluated, among other things, for providing a medical condition indication associated with the patient.

According to another embodiment, each of the plurality of coded regions may comprise graphical indicia such as color-coded sections.

According to yet another aspect, there is provided a computer implemented method of evaluating a measure of severity of illness in a patient, where the computer implemented method comprises entering by the computer an age range associated with the patient; assigning by the computer a plurality of coded regions to measurements associated with each of a plurality of vital signs based on the entered age range; measuring by the computer the plurality of vital signs associated with the patient; associating by the computer one of the plurality of code regions to each of the measured vital signs; assigning by the computer a score value to each of the associated plurality of coded regions; determining by the computer a total score from the score value assigned to each of the associated plurality of coded regions; determining by the computer a measure of the severity of illness based on the total score; and determining by the computer a care recommendation based on the measure.

According to one embodiment, the computer comprises using a processor based device, where using the processor based device may include using one or more of a personal digital assistant (PDA), a portable computer, a desktop computer, a server computer, etc.

According to still yet another aspect, there is provided a computer-readable medium embodying machine-readable code for preemptively evaluating a measure of severity of illness in a patient, where the machine-readable code comprises machine-readable code for determining an age range associated with the patient; machine-readable code for determining a plurality of vital signs; machine-readable code for assigning a plurality of coded regions to measurements associated with each of the determined plurality of vital signs based on the determined age range; machine-readable code for measuring the plurality of vital signs associated with the patient; machine-readable code for associating one of the plurality of coded regions to each of the measured vital signs; machine-readable code for assigning a score value to each of the associated plurality of coded regions; machine-readable code for determining a total score from the score value assigned to each of the associated plurality of coded regions; machine-readable code for determining a measure of the severity of illness based on the total score; and machine-readable code for determining a care recommendation based on the measure.

According to still yet another aspect, there is provided a vital sign evaluation tool for evaluating a measure of severity of illness associated with a patient, the tool comprising a displayed grid, said displayed grid comprising multiple groups of coded regions, each group of coded regions being assigned to a respective one of a plurality of vital signs, said vital signs comprising respiratory rate, heart rate, respiratory effort, oxygen therapy, capillary refill time, transcutaneous oxygen selection and systolic blood pressure, each of the plurality of coded regions being scaled according to one of a plurality of age ranges associated with the patient and adapted to generate a score value corresponding to a measurement of the vital sign, the score value within the plurality of the coded regions summed to produce a total score, wherein the total score is adapted to provide an indication of the severity of illness of the patient.

BRIEF DESCRIPTION OF THE DRAWINGS

Various embodiments will now be described more fully with reference to the accompanying drawings in which:

FIGS. 6A and 6B illustrate care recommendations corresponding to total scores generated using the vital sign evaluation tool of FIGS. 1A-3B;

DETAILED DESCRIPTION OF THE PREFERRED EMBODIMENT

In the following description, an embodiment of a vital sign evaluation tool, system and method for determining the severity of illness of patients, for example, in the pediatric field, is provided.

Figure 1A:
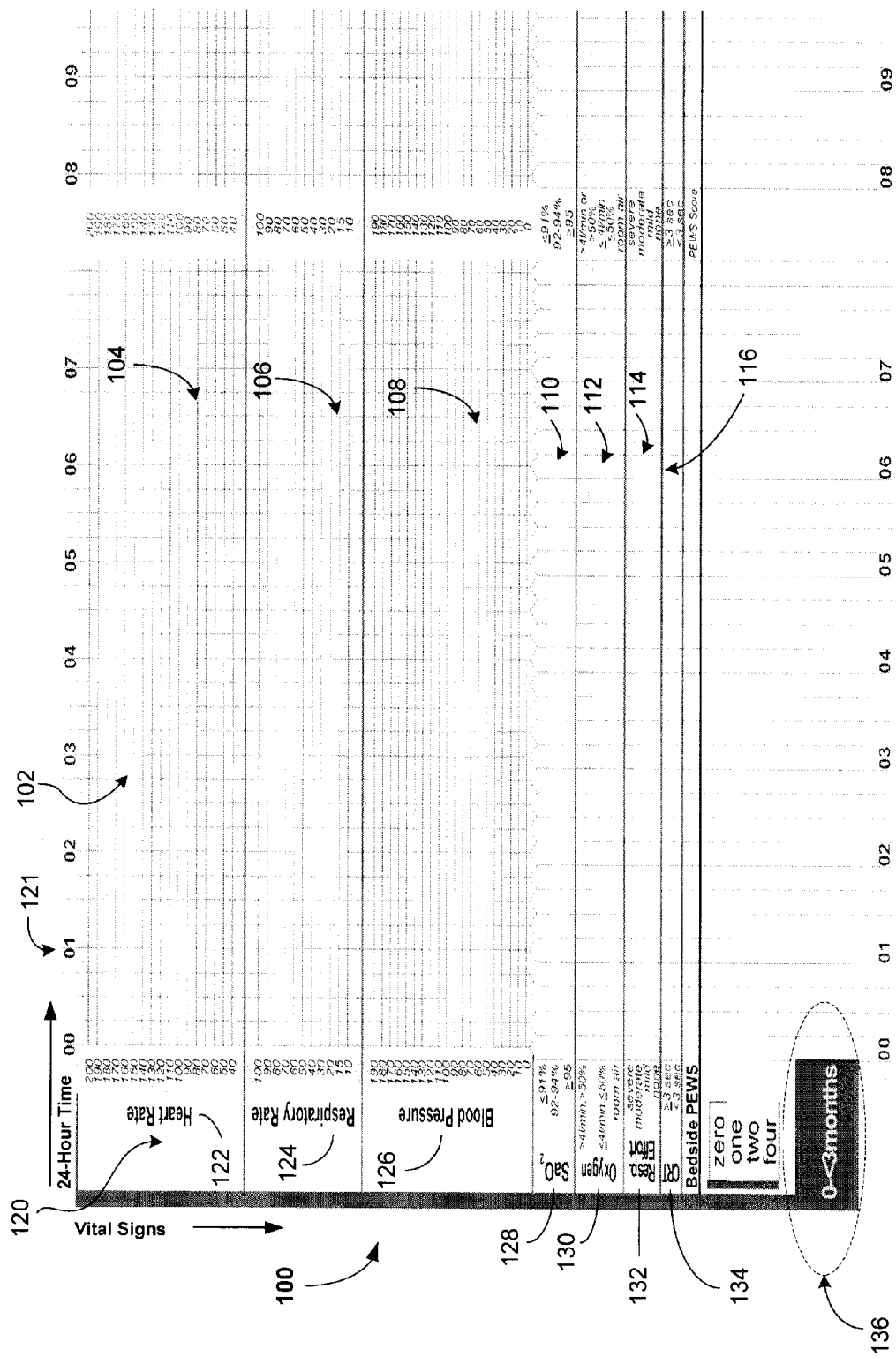
FIGS. 1A-3B illustrate a vital sign evaluation tool.

Turning now to FIG. 1A, a vital sign evaluation tool 100 for evaluating a measure of severity of illness associated with a patient is shown. The vital sign evaluation tool 100 includes a displayed grid 102 divided into a plurality of coded regions 104-116 each assigned to one of the vital signs indicated along vertical column 120. For example, coded region 104 corresponds to a heart rate measurement 122, coded region 106 corresponds to a respiratory rate measurement 124, coded region 108 corresponds to a blood pressure measurement 126, coded region 110 corresponds to a measure of transcutaneous oxygen saturation 128, coded region 112 corresponds to the level of provided oxygen therapy 130, coded region 114 corresponds to a measure of respiratory effort 132, and coded region 116 corresponds to a measure of capillary refill time 134. As indicated along horizontal axis 121, an indication of a 24-hour time period is displayed in order to allow vital sign measurements to be entered into the coded regions 104-116 at particular times in the 24-hour time period.

Each of the plurality of coded regions 104-116 is scaled according to one of a plurality of age ranges, where an age range indicator 136 provides the range of ages to which the grid 102 applies. For example, the age range indicator 136 may specify an age of 0 (i.e., newborn) to just under 3-months old.

Figure 1B:
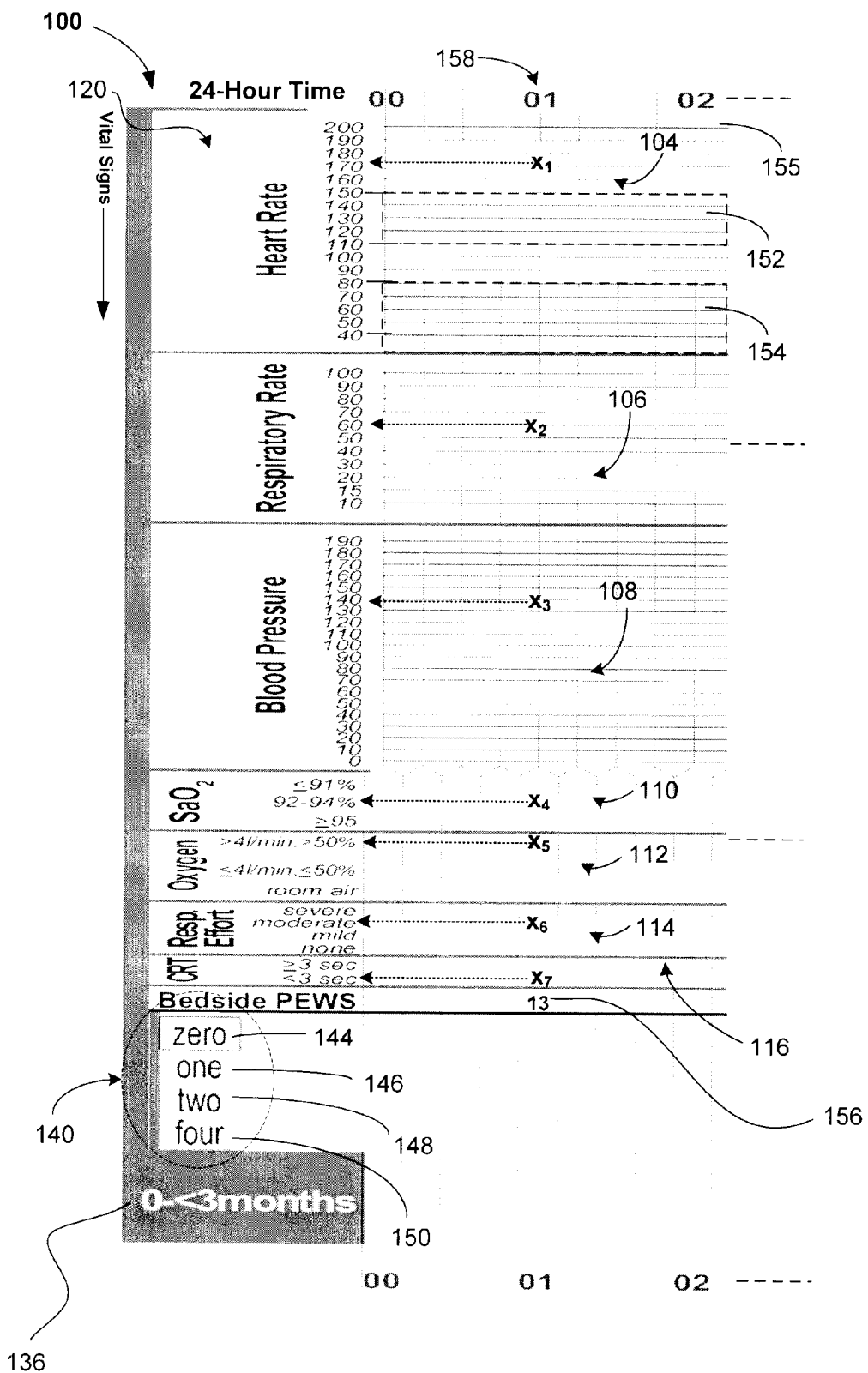

Turning to FIG. 1B, left side of the vital sign evaluation tool 100 is better illustrated. As can be seen, the vital sign evaluation tool 100 also includes a score value indicator 140 that provides a key for mapping one or more sections within each coded region 104-116 to a score value. For example, box 144 may include a color, shading, or graphical indicator that corresponds to a matching color, shading, or graphical indicator within each of coded regions 104-116. Similarly, boxes 146-150 may also include a color, shading, or graphical indicator that corresponds to a matching color, shading, or graphical indicator within each of coded regions 104-116. As illustrated, box 144, which corresponds to a score value of zero, is encoded as white. Therefore, any region within each of the coded regions 104-116 that is white is designated with a score value of zero. For example, within coded region 104, white section 152 includes a score value of zero (0), which corresponds to heart rate measurements ranging between 110-150 beats per minute. Also, in this example, box 150, which corresponds to a score value of 4, is encoded as a purple color. Thus, any region within each of the coded regions 104-116 that is purple is designated with a score value of 4. For example, within coded region 104, purple section 154 includes a score value of four (4), which corresponds to heart rate measurements ranging between 40-80 beats per minute. In the exemplary embodiments described herein, a lower score value is indicative of a less severe vital sign measurement. For example, for heart rate measurements, a score value of zero (0) is indicative of a normal heart rate. Conversely, a score value of four (4) is indicative of an abnormally high or low heart rate. As indicated within coded region 104, abnormally low heart rates are designated as purple section 154, while abnormally high heart rates are represented by purple section 155, which is indicative of a heart rate range of 190-200 beats per minute.

In operation, the vital sign evaluation tool 100 may be utilized for generating a score value corresponding to each of vital signs associated with column 120. The generated score values associated with each of the vital signs within coded regions 104-116 are summed to produce a total score, whereby the total score is adapted to provide an indication of the severity of illness of the patient.

For example, as shown in FIG. 1B, a user of the vital sign evaluation tool 100 may, at a particular time, enter various vital sign measurements associated with a patient into the evaluation tool 100 in order to generate a total score. Within the coded region 104 corresponding to heart rate measurements, $x_1$ marks a heart rate measurement of 170 beats per minute taken from the patient at a time of 1 am, as indicated at 158. As illustrated, the position of $x_1$ corresponds to a color (i.e., yellow) that matches box 146, which is indicative of a score value of one (1). Within the coded region 106 corresponding to respiratory rate measurements, $x_2$ marks a respiratory rate of 60 per minute taken from the patient at a time of 1 am, as indicated at 158. As illustrated, the position of $x_2$ corresponds to a color (i.e., yellow) that matches box 146, which is indicative of a score value of one (1). Also, within the coded region 108 corresponding to blood pressure measurements, $x_3$ marks a blood pressure measurement of 130 taken at a time of 1 am, as indicated at 158. As illustrated, the position of $x_3$ corresponds to a color (i.e., purple) that matches box 150, which is indicative of a score value of four (4). Within the coded region 110 corresponding to transcutaneous oxygen saturation, $x_4$ marks a transcutaneous oxygen saturation level of between 93-94% taken at a time of 1 am, as indicated at 158. The position of $x_4$ corresponds to a color (i.e., yellow) that matches box 146, which is indicative of a score of one (1). Within the coded region 112 corresponding to oxygen therapy level, $x_5$ marks an oxygen therapy of greater than 4 liters per minute at a concentration level of greater than 50% taken at a time of 1 am, as indicated at 158. The position of $x_5$ corresponds to a color (i.e., purple) that matches box 150, which is indicative of a score of four (4). Within the coded region 114 corresponding to the measure of respiratory effort, $x_6$ marks a moderate respiratory effort taken at a time of 1 am, as indicated at 158. The position of $x_6$ corresponds to a color (i.e., pink) that matches box 148, which is indicative of a score of two (2). Finally, within the coded region 114 corresponding to the capillary refill time, $x_7$ marks a capillary refill time of less than three seconds (<3) taken at a time of 1 am, as indicated at 158. The position of $x_7$ corresponds to a color (i.e., white) that matches box 144, which is indicative of a score of zero (0). Thus, at a time of 1 am, the total score is determined by adding the score values corresponding to $x_1$-$x_7$, which equates to a total score of thirteen (i.e., 1+1+4+1+4+2+0=13), as indicated at 156. In pediatric care environments (e.g., pediatric ward of a hospital), this total score may be designated as a Pediatric Early Warning System (PEWS) score value.

Figure 2A:
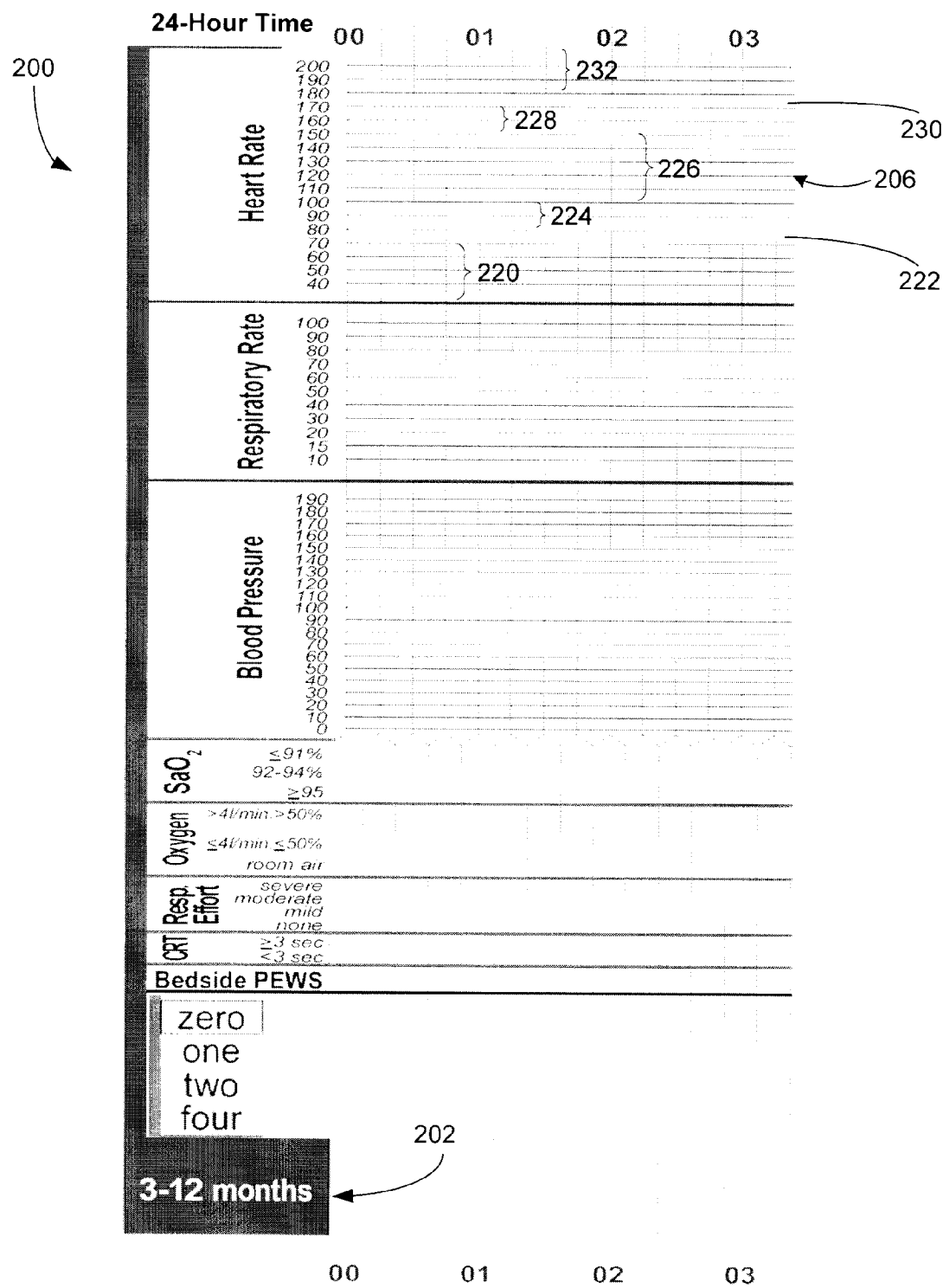
Figure 3A:
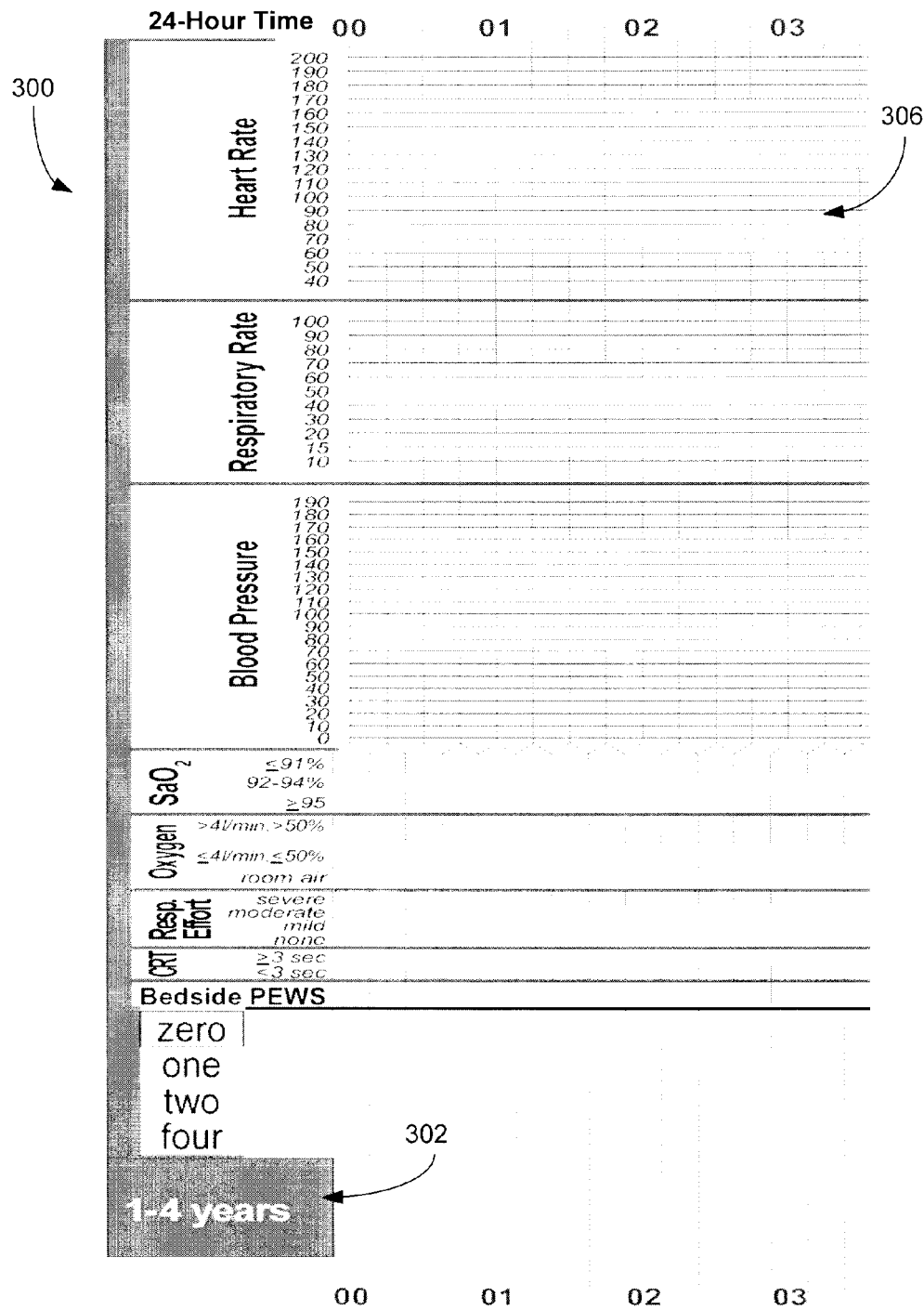

While the vital sign evaluation tool 100 of FIG. 1A evaluates a measure of severity of illness for patients in the age range of 0-3 months, FIG. 2A illustrates a vital sign evaluation tool 200 for evaluating a measure of severity of illness associated with a patient in the age range of 3-12 months, as indicated by age range indicator 202. Similarly, FIG. 3A is a vital sign evaluation tool 300 for evaluating a measure of severity of illness associated with a patient in the age range of 1-4 years, as indicated by age range indicator 302. Although the layout and features of vital sign evaluation tools 100, 200, and 300 are similar, the assignment of score values to the different ranges of vital sign within each coded region vary according to each vital sign evaluation tool 100, 200, 300.

Figure 1C:
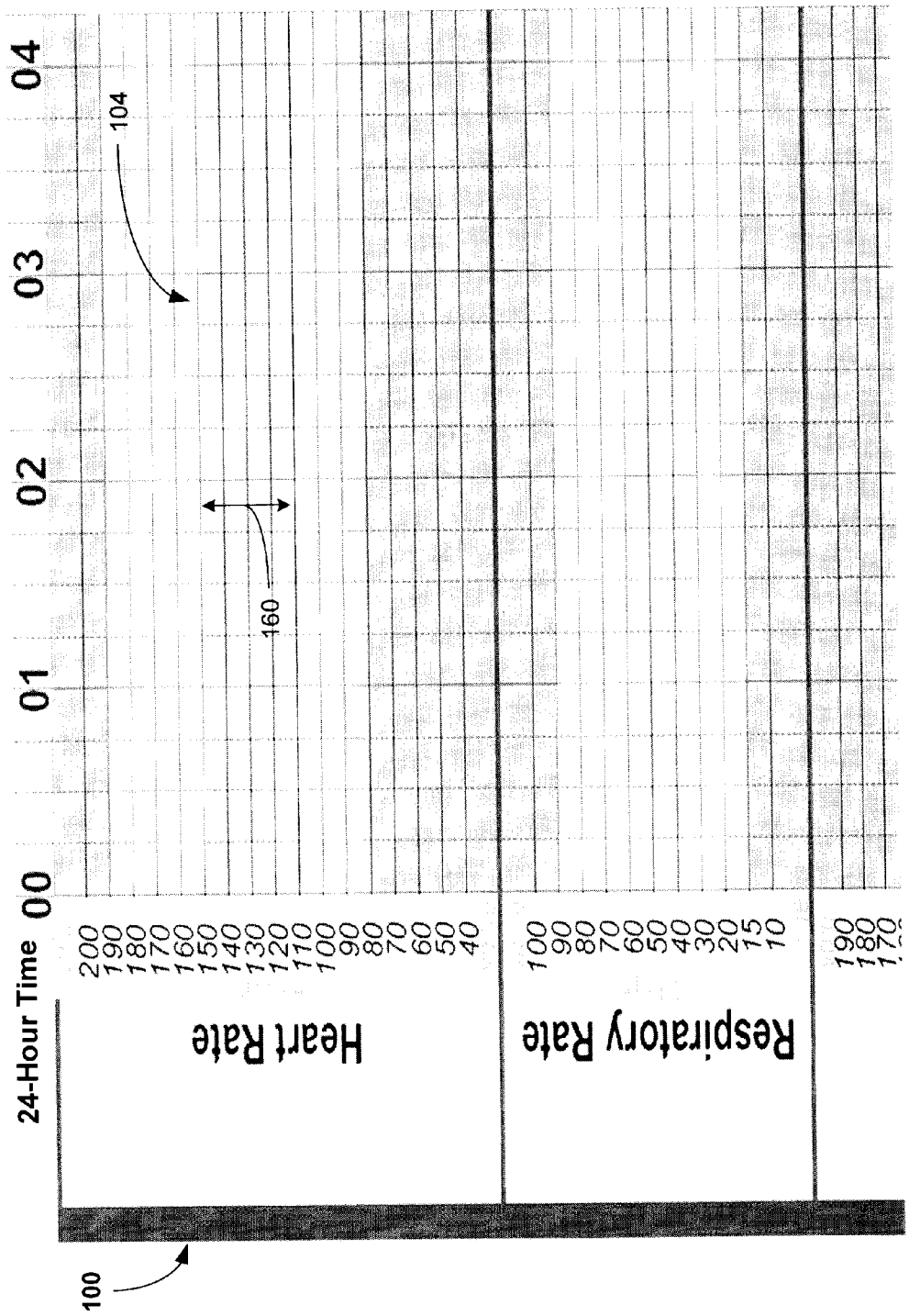
Figure 2B:
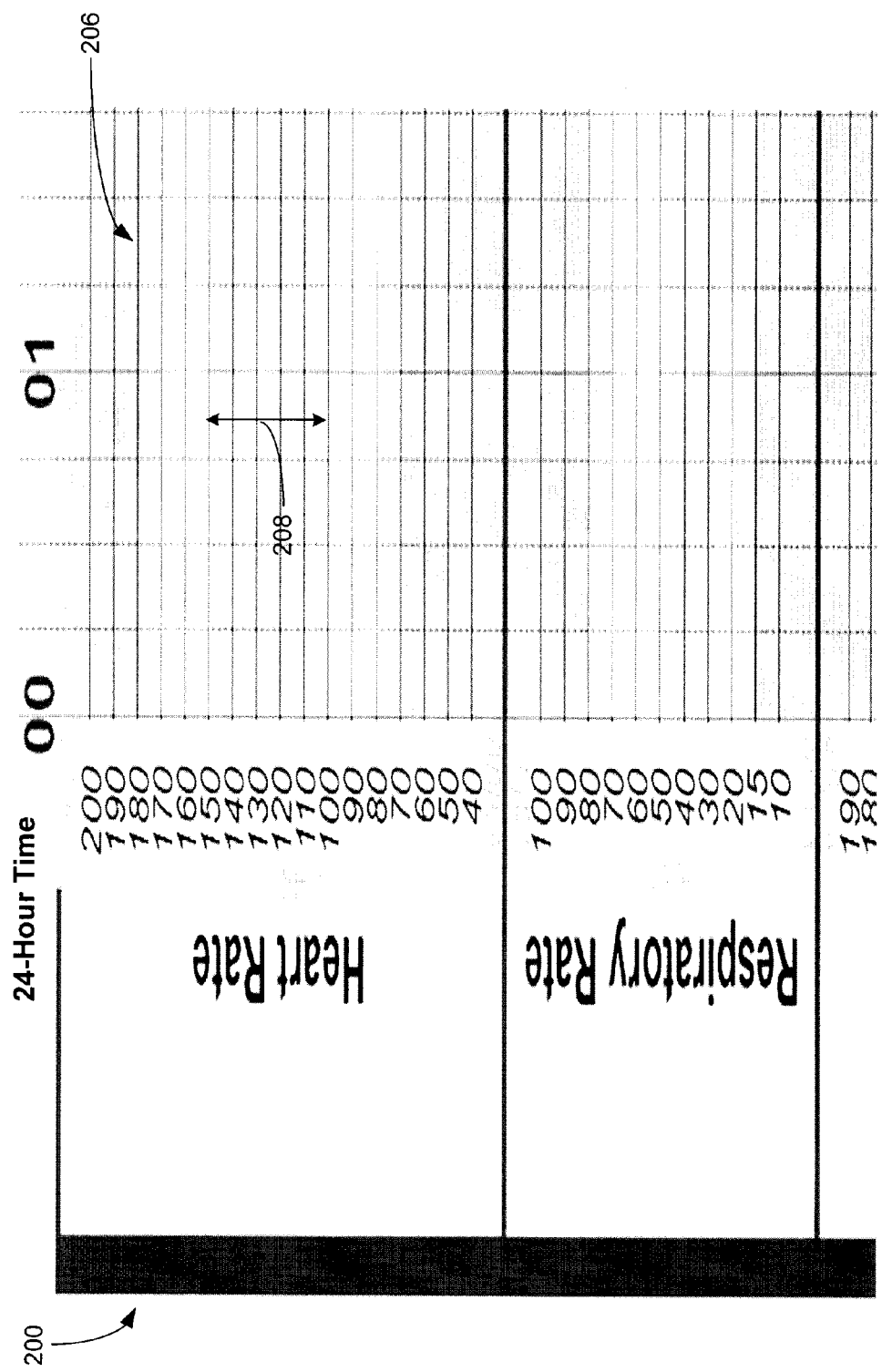
Figure 3B:
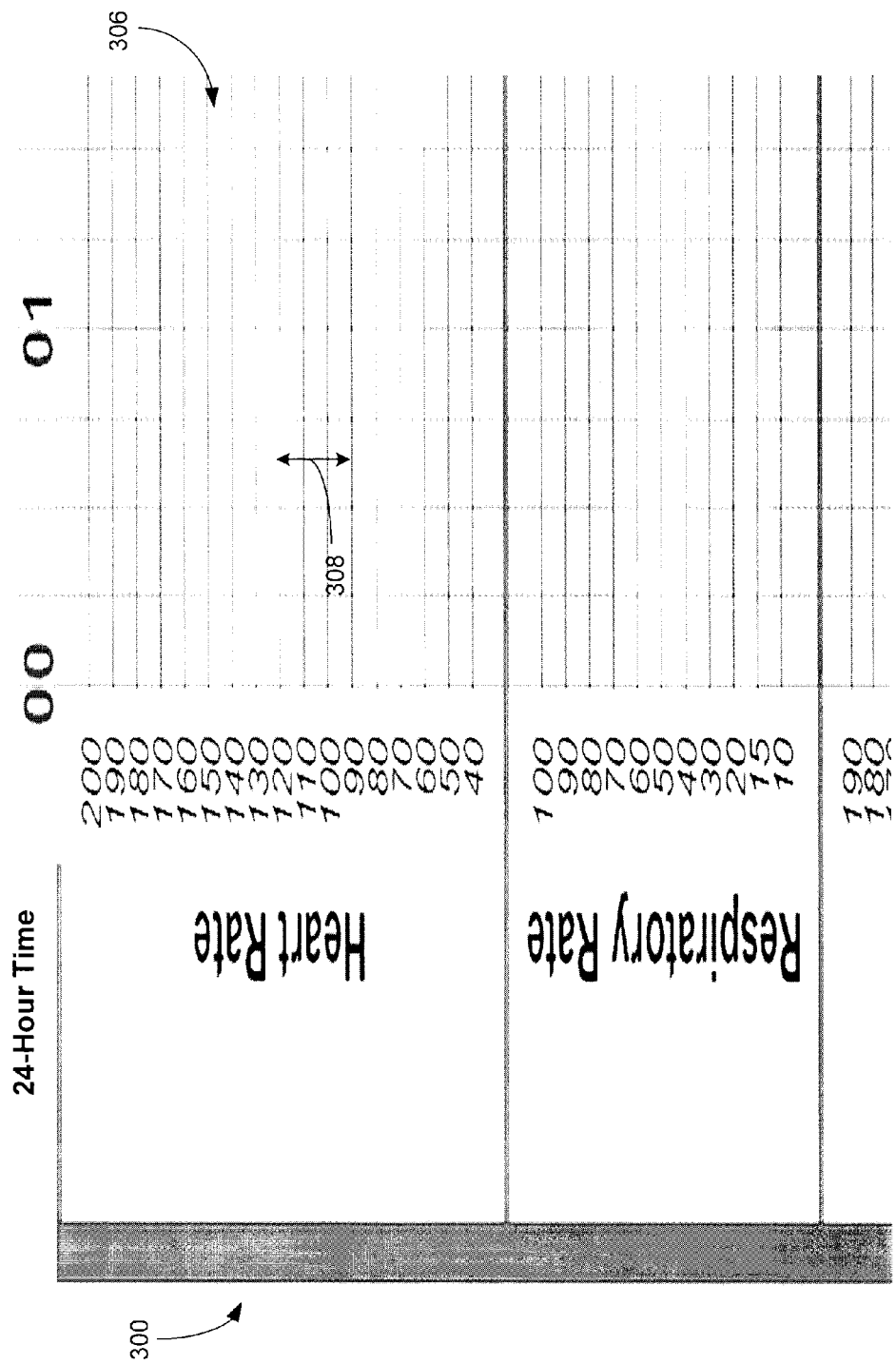

For example, referring to FIGS. 1C, 2B, and 3B, the assignment of score values within the coded regions associated with the heart rate and respiratory rate vital signs of the vital sign evaluation tools 100, 200 and 300 are shown. As can be seen, in the 0-3 month age range, as indicated in FIG. 1C, a score of zero (0) within the coded region 104 for the heart rate measurement is assigned to a range of heart rate measurements corresponding to 110-150 beats per minute, as indicated at 160. In the 3-12 months age range, FIG. 2B illustrates a score of zero (0) in coded region 206 for a range of heart rate measurements corresponding to 100-150 beats per minute, as indicated at 208. In the 1-4 years age range, FIG. 3B illustrates a score of zero (0) in coded region 306 for a range of heart rate measurements corresponding to 90-120 beats per minute, as indicated at 308. Thus, in order to calculate a more accurate scoring system, each vital sign measurement and its designated score value is tailored to a particular range of ages. For example, in the older age group of 1-4 years, a score value of zero (0) corresponds to a narrower range of heart rate measurements in comparison to the heart rate measurements corresponding to the 0-3 and 3-12 month age ranges.

Once a total score has been calculated for a patient, this total score is compared to a predetermined threshold in order to initiate an appropriate medical response or assign/dispatch the appropriate medical resources (e.g., number of nurses on ward, designated medical teams, etc.). Determination of threshold values and scores may be provided based on the steps illustrated in flowchart 600 of FIG. 6, as described below. For example, based on the total score value, an immediate assessment, an urgent assessment, or a routine assessment of the patient is initiated by scheduling and dispatching the appropriate medical personnel (e.g., one or more nurses and/or doctors) or team (e.g., team of doctors and/or nurses).

If desired, the vital sign evaluation tool may be embodied as computer program code stored on a tangible computer readable medium and displayed on a graphical user interface when executed by suitable processing structure. In this case, measured vital signs can be entered into the processing structure in order to determine score values and calculate total scores. The operational steps for determining the total score using vital sign indication tools 100 (FIGS. 1A-1C), 200 (FIGS. 2A-2B), and 300 (FIGS. 3A-3B) when embodied as computer program code may be found in the operational flow chart 400 of FIG. 4.

Figure 4:
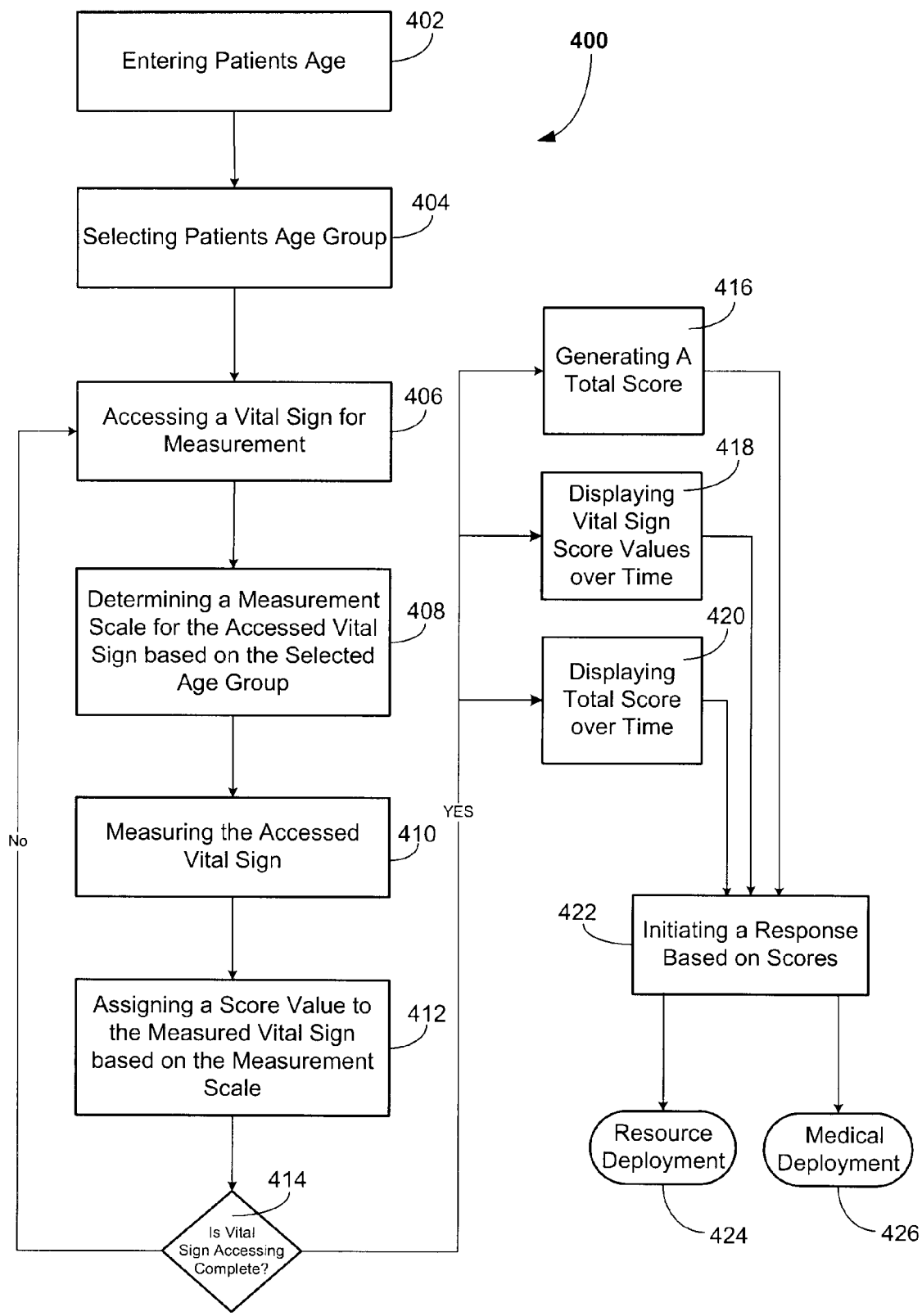
FIG. 4 is a flow diagram corresponding to the operation of the vital sign evaluation tool of FIGS. 1A-3B when embodied as computer program code.

Turning now to FIG. 4, during execution of the vital sign evaluation tool computer program code, at step 402 a patient's age is entered in order to select the patient's age group (step 404). For example, if an age of 5 months is entered, an age group or range of 3-12 months is selected. At step 406, a vital sign (e.g., heart rate) is accessed for measurement, whereby based on the selected age group (step 404), a measurement scale associated with the accessed vital sign is determined (step 408). For example, referring to FIG. 2A, based on the selected age group of 3-12 months, the determined measurement scale for the heart rate includes a 40-70 beats per minute range 220 corresponding to a score value of four (4), a 70-80 beats per minute range 222 corresponding to a score value of two (2), an 80-100 beats per minute range 224 corresponding to a score value of one (1), a 100-150 beats per minute range 226 corresponding to a score value of zero (0), a 150-170 beats per minute range 228 corresponding to a score value of one (1), a 170-180 beats per minute range 230 corresponding to a score value of two (2), and a 180-200 beats per minute range 232 corresponding to a score value of four (4). For each accessed vital sign, based on age range, a measurement scale is determined for the vital sign (step 408).

At step 410, a vital sign measurement corresponding to the accessed vital sign (e.g., heart rate) is taken from the patient. Once the vital sign measurement is taken (step 410), it is assigned a score value (step 412) based on the measurement scale (step 408) associated with the accessed vital sign (step 406). For example, referring to FIG. 2B, a heart rate vital sign measurement of "60" beats per minute falls within the 40-70 beats per minute range 220 for the accessed heart rate vital sign, which corresponds to a score value of four (4).

A check is then made to determine if any other vital sign is to be measured (step 414). If so, the process reverts back to step 406 and steps 406 to 412 are re-performed for each additional vital sign to be measured. Once it is determined that no other vital sign is to be measured at step 414, a total score is calculated by summing all the determined score values associated with their respective vital signs is generated (step 416). Also, at step 418, each score value associated with each individual vital sign (step 412) may be displayed at various time periods (e.g., 1 am, 2 am, 3 am, . . . ), for example using a graph. At step 420, the calculated total scores (step 416) may also be display at various time periods (e.g., 1 am, 2 am, 3 am, . . . ). Steps 418 and 420 may enable a medical professional to monitor the displayed changes in severity illness over time based on either or both the individual score values for a particular vital sign and/or the total scores generated for a group of vital signs. If it is determined that one or more other vital signs associated with the patient are to be measured (step 414), the process returns to step 406 and progresses through steps 408-414.

Once the scores (i.e., individual and total) from steps 416, 418, and 420 are calculated and optionally displayed, based on the score values and/or the changes in the scores a response may be initiated (step 422). For example, based on the total score value for one or more patients being at or above a certain value or within a particular range of values, various resources (e.g., nurses, monitoring equipment, etc.) may be deployed (step 424). In one instance, if the average total score for the patients on a hospital ward exceeds a predetermined threshold value, the number of nursing staff may be increased. In another instance, exceeding the threshold may initiate the deployment of a particular medical team or medical personnel to the ward (step 422).

Figure 5A:
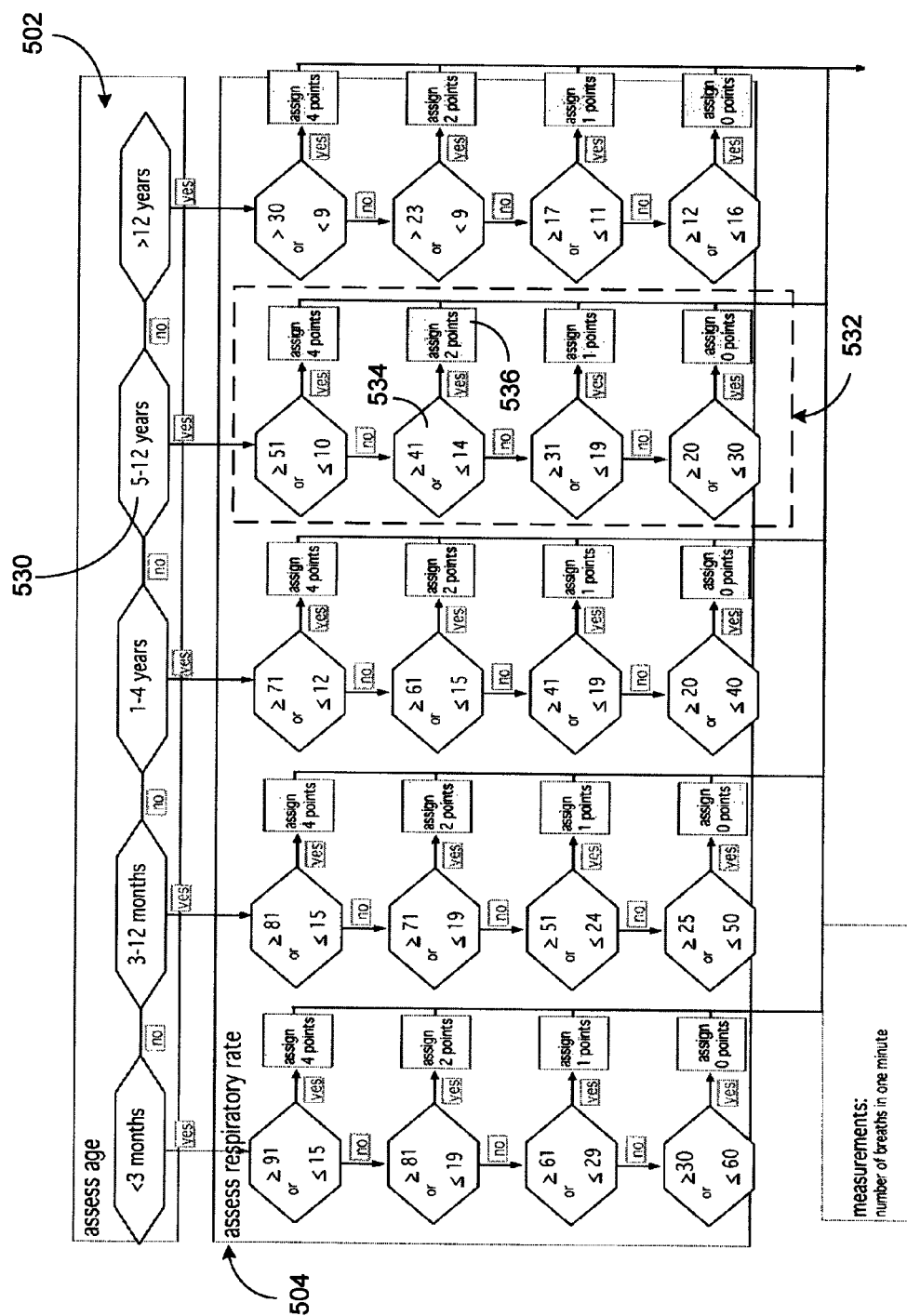
FIGS. 5A-5G are exemplary flow diagrams illustrating total score value calculation steps.
Figure 5B:
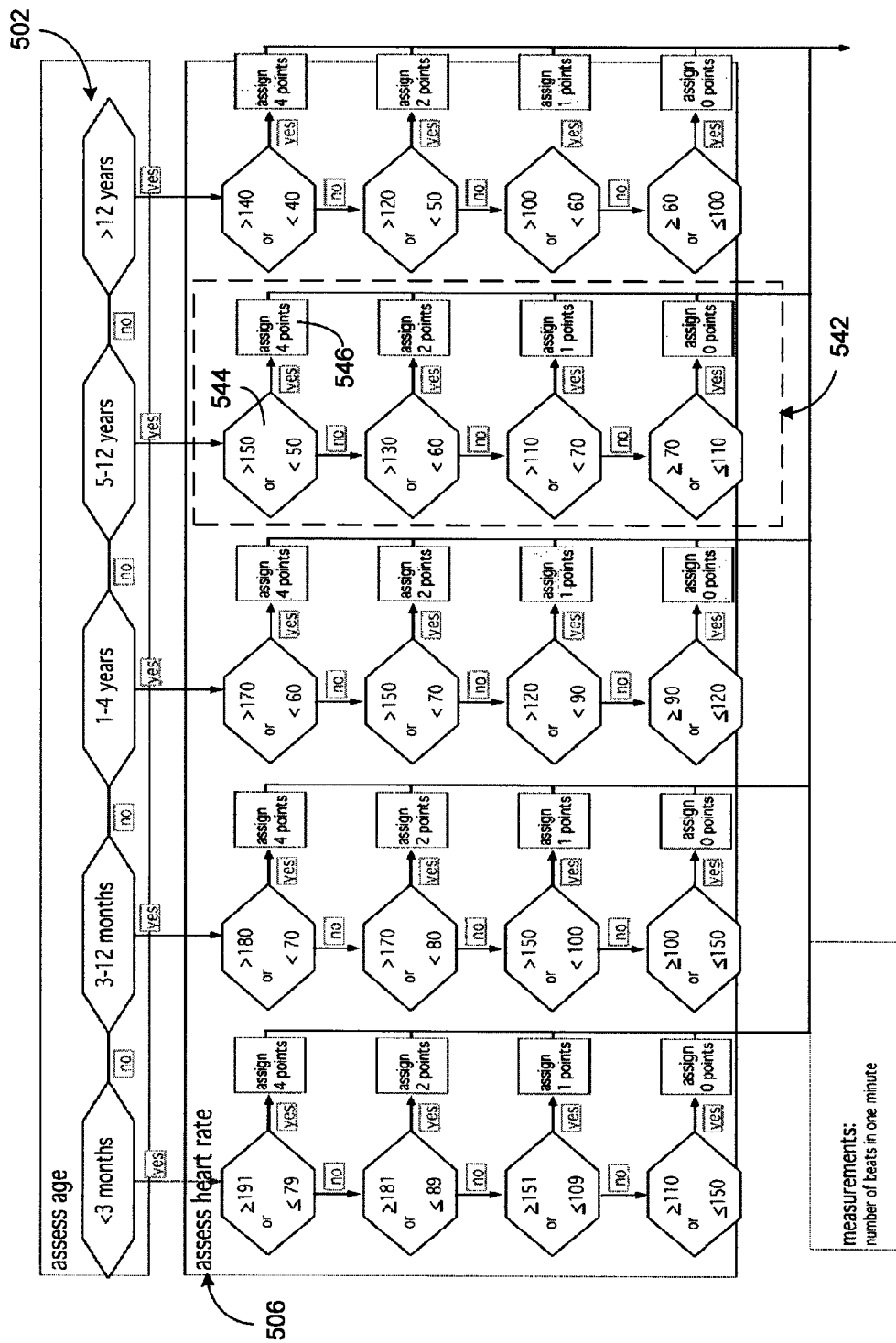
Figure 5C:
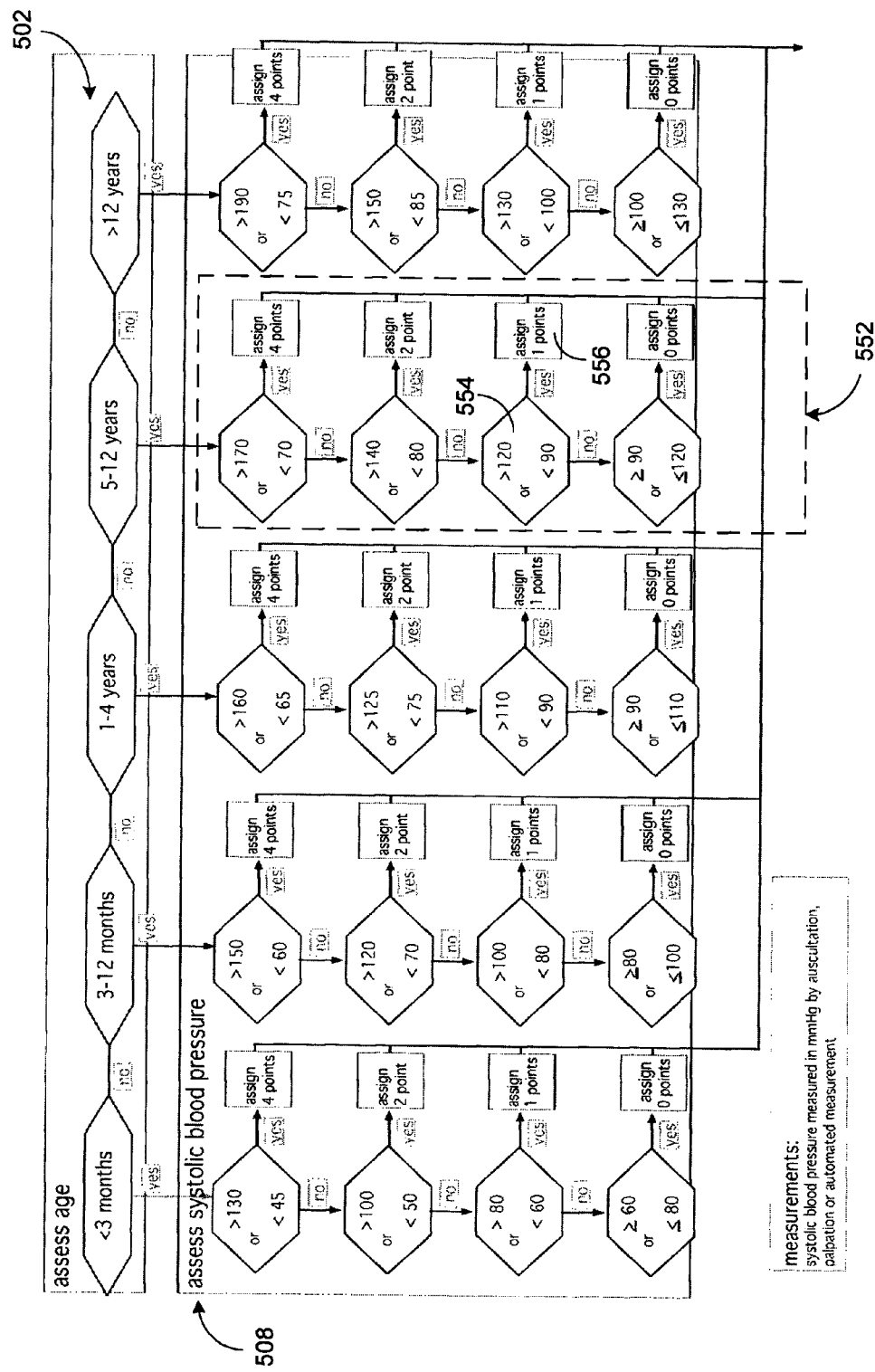
Figure 5D:
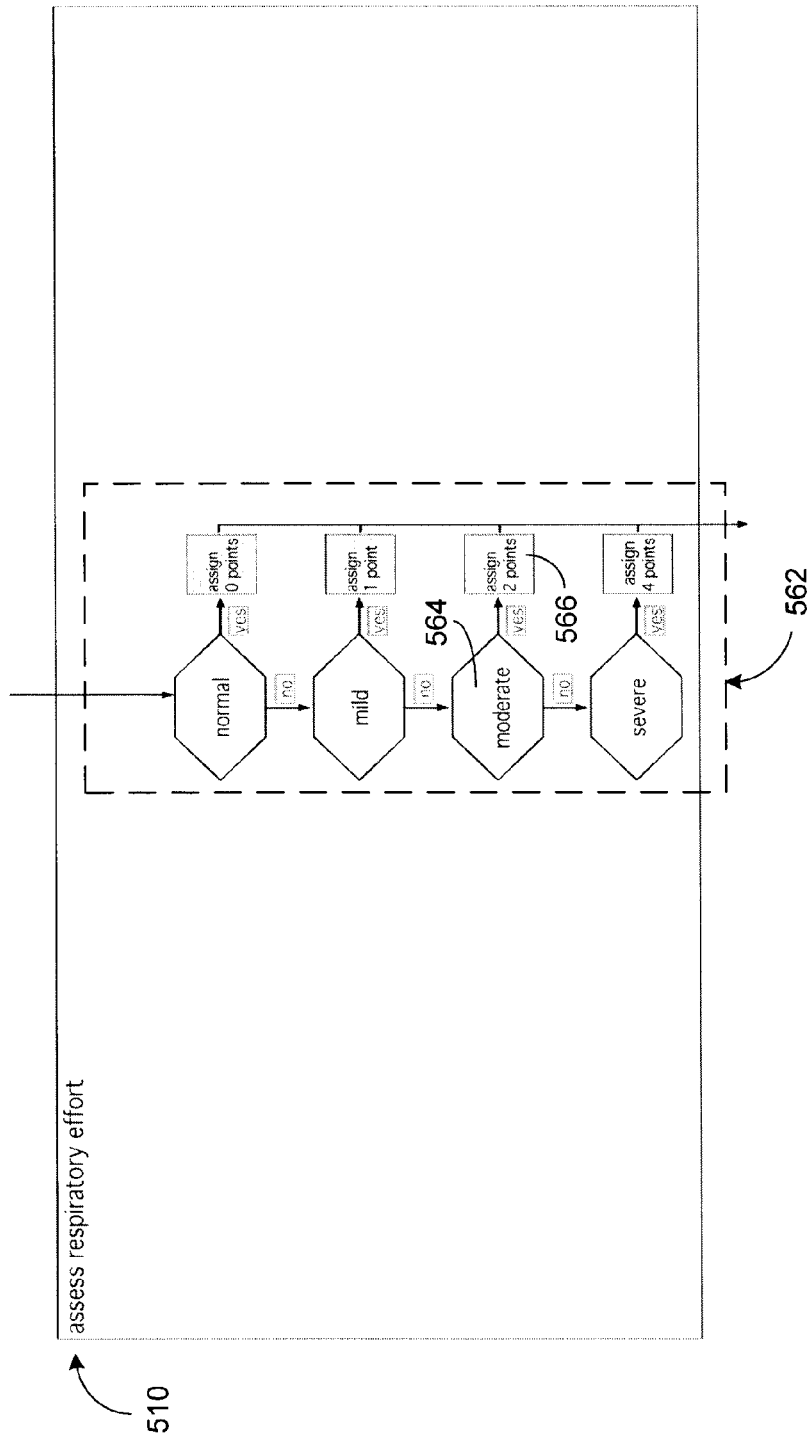
Figure 5E:
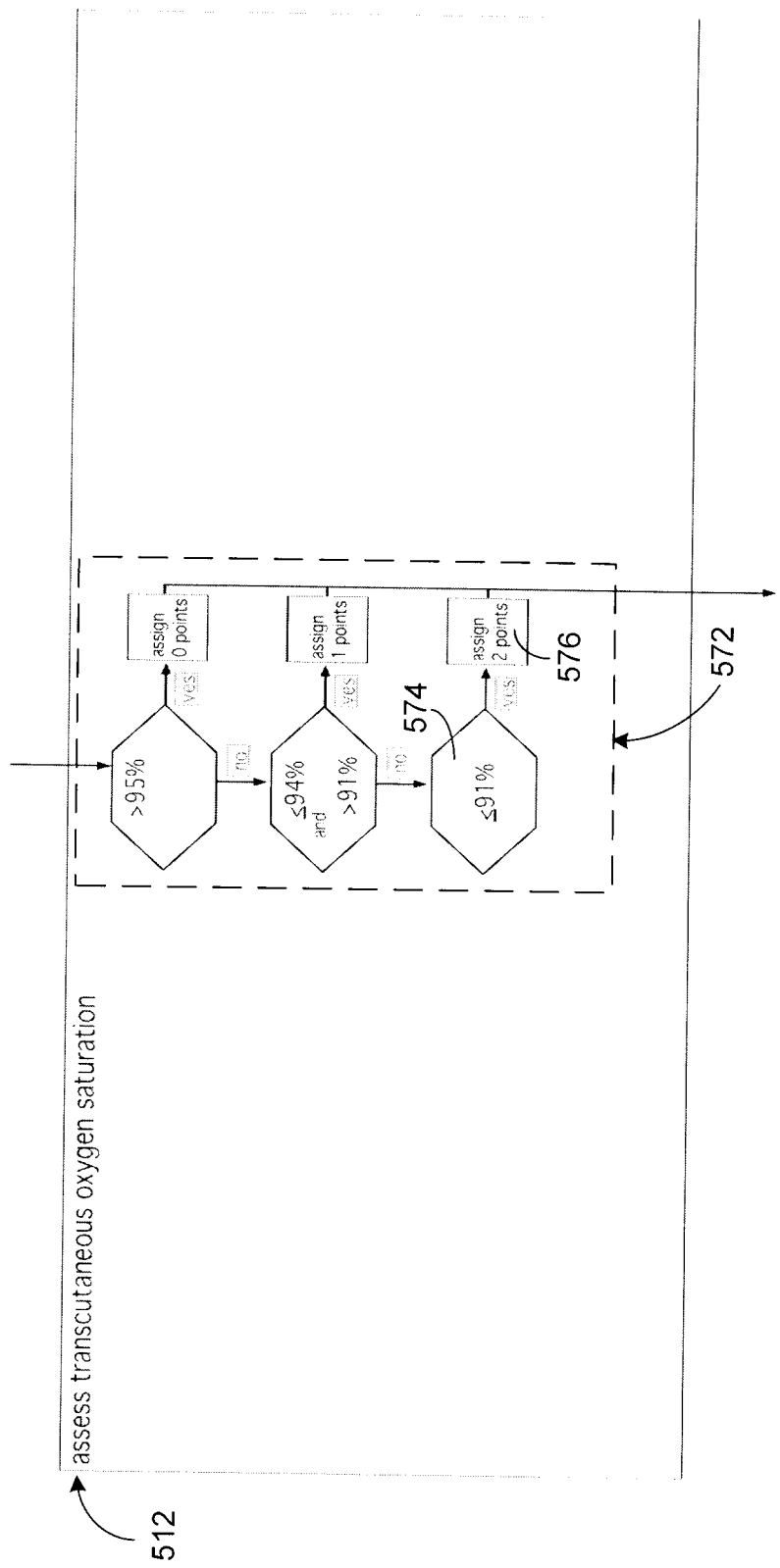
Figure 5F:
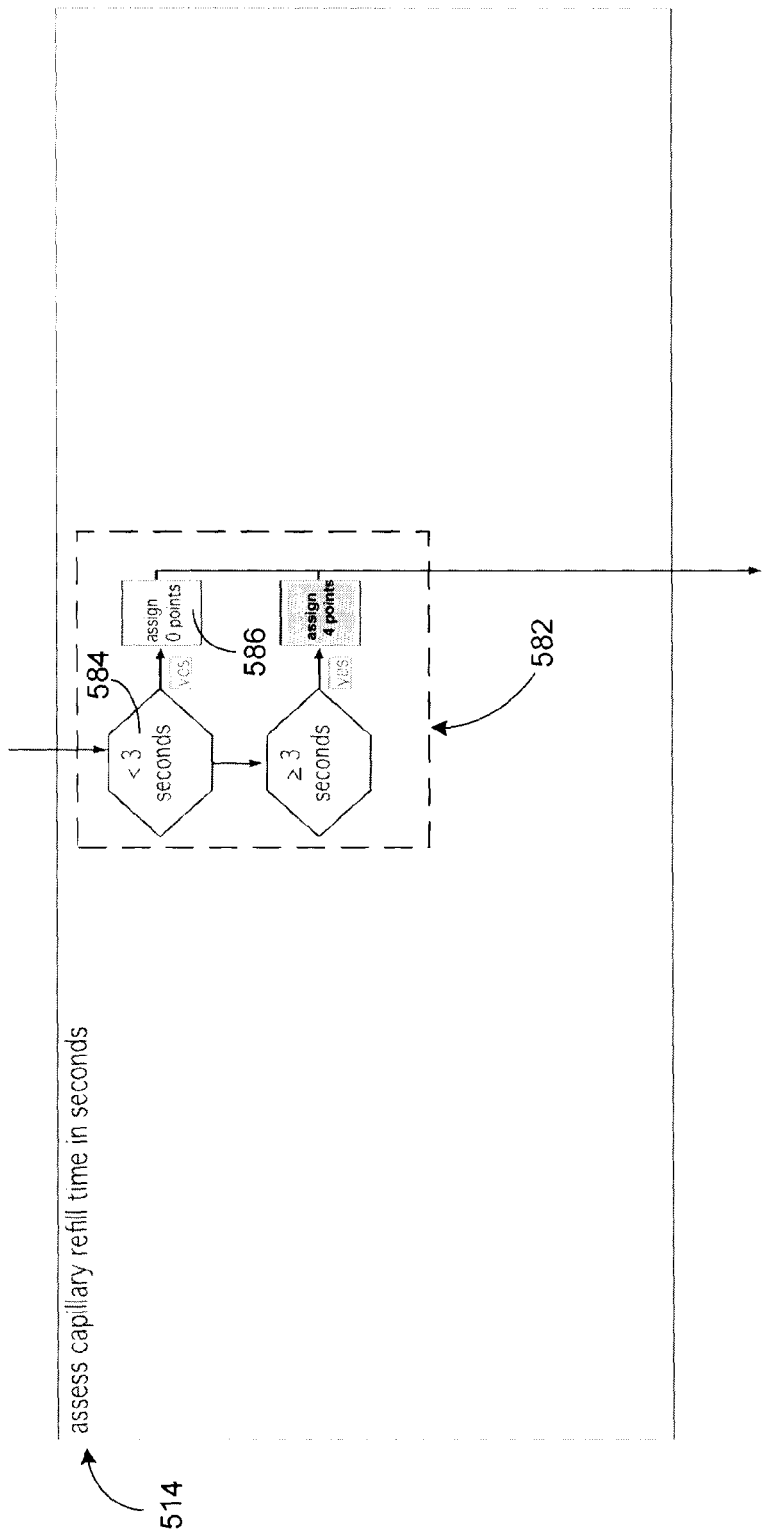
Figure 5G:
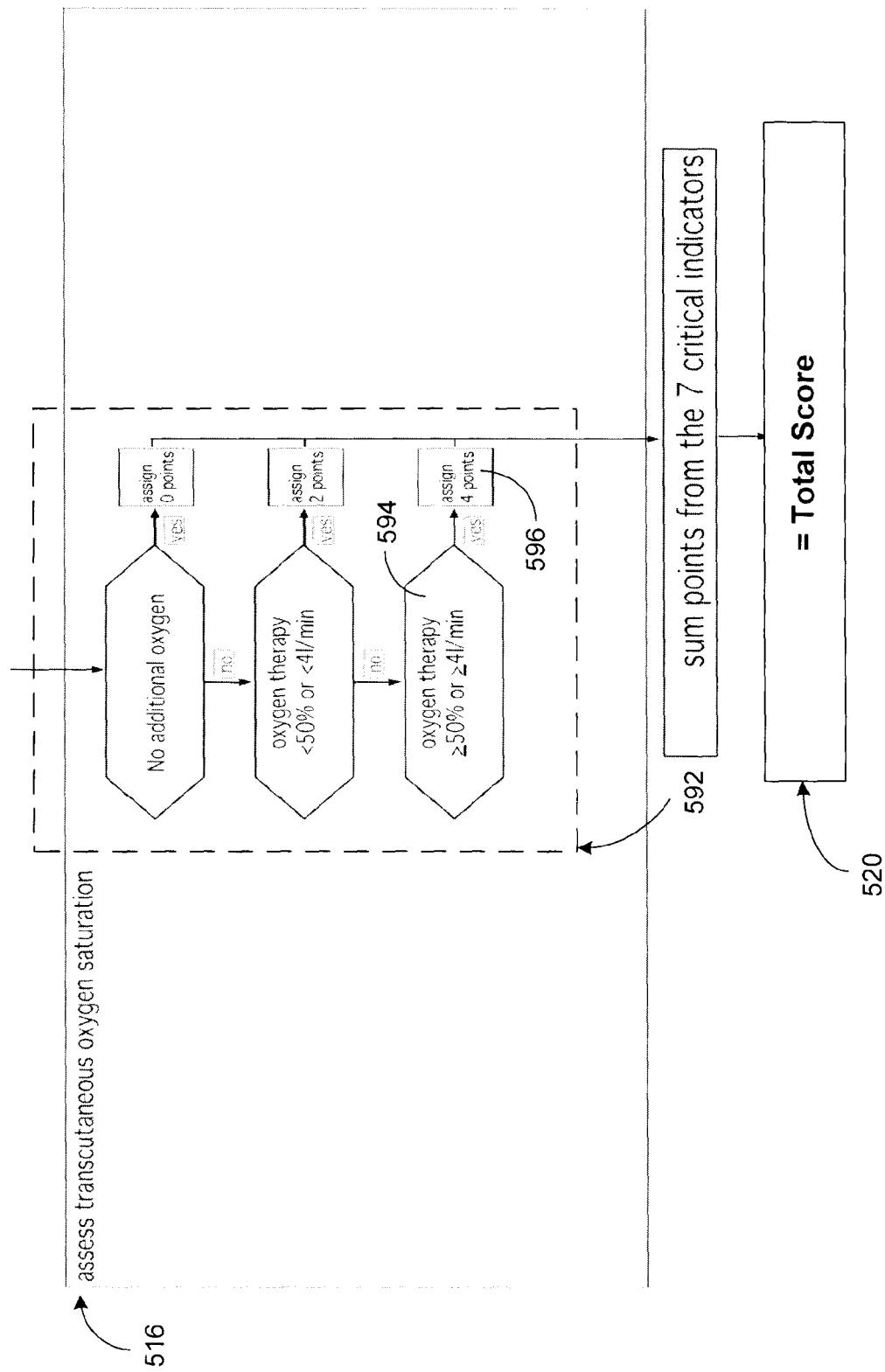

FIGS. 5A-5G are exemplary flow diagrams illustrating the total score calculation steps associated with the vital sign evaluation tool. As illustrated, for various age ranges 502, based on the entered vital sign measurements 504-516, a particular score value (i.e., assigned points) is allocated. Once the scores for each of the vital signs 504-516 have been allocated, a total score is computed, as indicated at 520 (FIG. 5G).

For example in FIG. 5A, if it is determined that a patient's age lies within the range of 5-12 years, as indicated at 530, for the respiratory rate vital sign, several ranges of measurement values corresponding to assigned scores or points are then accessed based on the 5-12 years age range, as indicated at 532. For example, if the measured respiratory rate is "42" and falls within range 534, a score value of two (2) is assigned, as indicated at 536.

Referring to FIG. 5B, for the heart rate vital sign, several ranges of measurement values corresponding to assigned scores or points are accessed based on the 5-12 years age range, as indicated at 542. For example, if the measured heart rate is "155" and therefore falls within range 544, a score value of four (4) is assigned, as indicated at 546.

Referring to FIG. 5C, for the systolic blood pressure vital sign, several ranges of measurement values corresponding to assigned scores or points are accessed based on the 5-12 years age range, as indicated at 552. For example, if the blood pressure is "125" and therefore falls within range 554, a score value of one (1) is assigned, as indicated at 556.

Referring to FIG. 5D, for the respiratory effort vital sign, several ranges of measurement values corresponding to assigned scores or points are accessed based, as indicated at 562. For example, if the respiratory effort is "moderate" and therefore falls within range 564, a score value of two (2) is assigned, as indicated at 566.

Referring to FIG. 5E, for the transcutaneous oxygen saturation vital sign, several ranges of measurement values corresponding to assigned scores or points are accessed, as indicated at 572. For example, if the transcutaneous oxygen saturation is "89%" and therefore falls within range 574, a score value of two (2) is assigned, as indicated at 576.

Referring to FIG. 5F, for the capillary refill time vital sign, several ranges of measurement values corresponding to assigned scores or points are accessed, as indicated at 582. For example, if the capillary refill time is "2 seconds" and therefore falls within range 584, a score value of zero (0) is assigned, as indicated at 586.

Referring to FIG. 5G, for the transcutaneous oxygen saturation vital sign, several ranges of measurement values corresponding to assigned scores or points are accessed, as indicated at 592. For example, if the oxygen therapy is "55%" or "5 L/Min" and therefore falls within range 594, a score value of four (4) is assigned, as indicated at 596.

In the above example, the total score value for these seven vital signs are: (2)+(0)+(2)+(2)+(1)+(4)+(2)=13. Based on this total score value a care recommendation or response may or may not be initiated. For example, if the total score value exceeds a certain threshold, a medical evaluation may be initiated in order to preemptively prevent any further deterioration of the patient's condition. In another example, if the total score values tend to climb over time, based on the gradient of the climb, deployment of medical staff, equipment, and/or medical response teams may be deemed necessary and thus initiated.

FIGS. 6A and 6B show possible care recommendations corresponding to total scores generated using the vital sign evaluation tool 100, 200 and 300. The care recommendations in FIG. 6A have been found to be suitable for community hospitals while those in FIG. 6B are tailored to teaching hospitals.

The process steps described and illustrated in relation to the exemplary flow diagrams of FIGS. 4 and 5A-5G may be implemented within any handheld, portable, or static processing device such as a server computer, a desktop computer, a laptop computer, a personal digital assistant, a piece of medical equipment, and/or any combination thereof that may be functioning within a communication network or as a standalone device. The functionality of the process steps may be implemented as a software program (e.g., C++ language) or any other form of coding (e.g., VHDL language), and loaded into any such devices for execution. A processing device may include, but is not limited to, a device that includes one or more processing devices (e.g., a custom application specific integrated circuit (ASIC), a field gate programmable array (FPGA) device, a microcontroller, a microprocessor, or any other programmable integrated circuit device).

Turning now to FIG. 6, a flow diagram 600 indicative of an exemplary method of assigning score values and score thresholds associated with the vital sign evaluation tool is provided. At step 602, an expert panel consisting of, for example, doctors, nurses, medical administrators, and other professionals associated with the medical field is formed. Interactive discussions are then carried out within the expert panel for the purpose of, among other things, identifying various clinical vital signs (step 604) such as blood pressure, heart rate, etc.

At step 606, using the expert panel, a number of clinically important age ranges (e.g., 0-3 months, 3-12 months, 1-4 years, etc.) corresponding to the identified vitals signs is determined. Similarly, clinically important measurement ranges are also determined for each vital sign within each determined age range (step 608).

At step 610, clinical data is obtained from a sample group of patients that fall within each of the determined age ranges, where the clinical data corresponds to measurements that are carried out for each of the vital signs identified by the expert panel. The expert panel then assigns score values to each of the measured vital signs based on where they fall within the identified measurement ranges for a particular age group (step 612).

At step 614, a total score value is determined for each of the patients in the sample group, whereby based on each vital sign measurement, a score value is assigned to the measured vital sign depending on what measurement range the measured vital sign falls within. The score values are then summed to calculate the total score value for the patient within the sample group.

At step 616, within the sample group, total score values associated with patients that have undergone an adverse event (e.g., cardiac arrest, etc.) are compared to total score values associated with patients that have not experienced such adverse events or medical conditions. Based on the results of the comparison (step 616), clinical thresholds for providing different responses may be determined (step 618), where a response may include, for example, performing an immediate assessment of the patient (e.g., code blue medical team dispatching), performing an urgent assessment of the patient (e.g., dispatching one or more physicians for determining the situation), or performing a routine assessment of the patient (e.g., via nurses doing their rounds on a ward).

Figure 7:
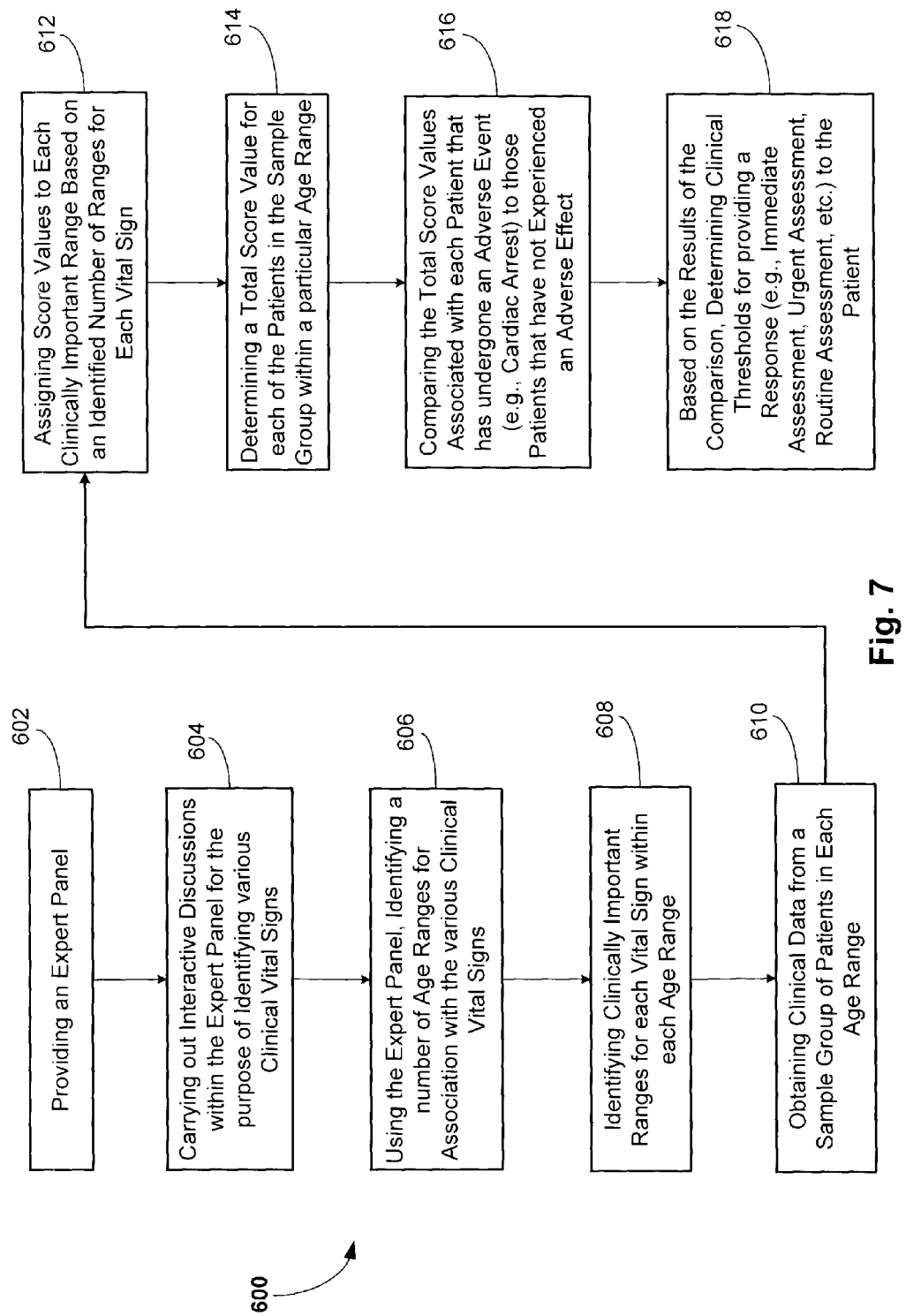
FIG. 7 is a flow diagram indicative of an exemplary method of assigning score values and score thresholds associated with the vital sign evaluation tool of FIGS. 1A-3B.
Figure 8:
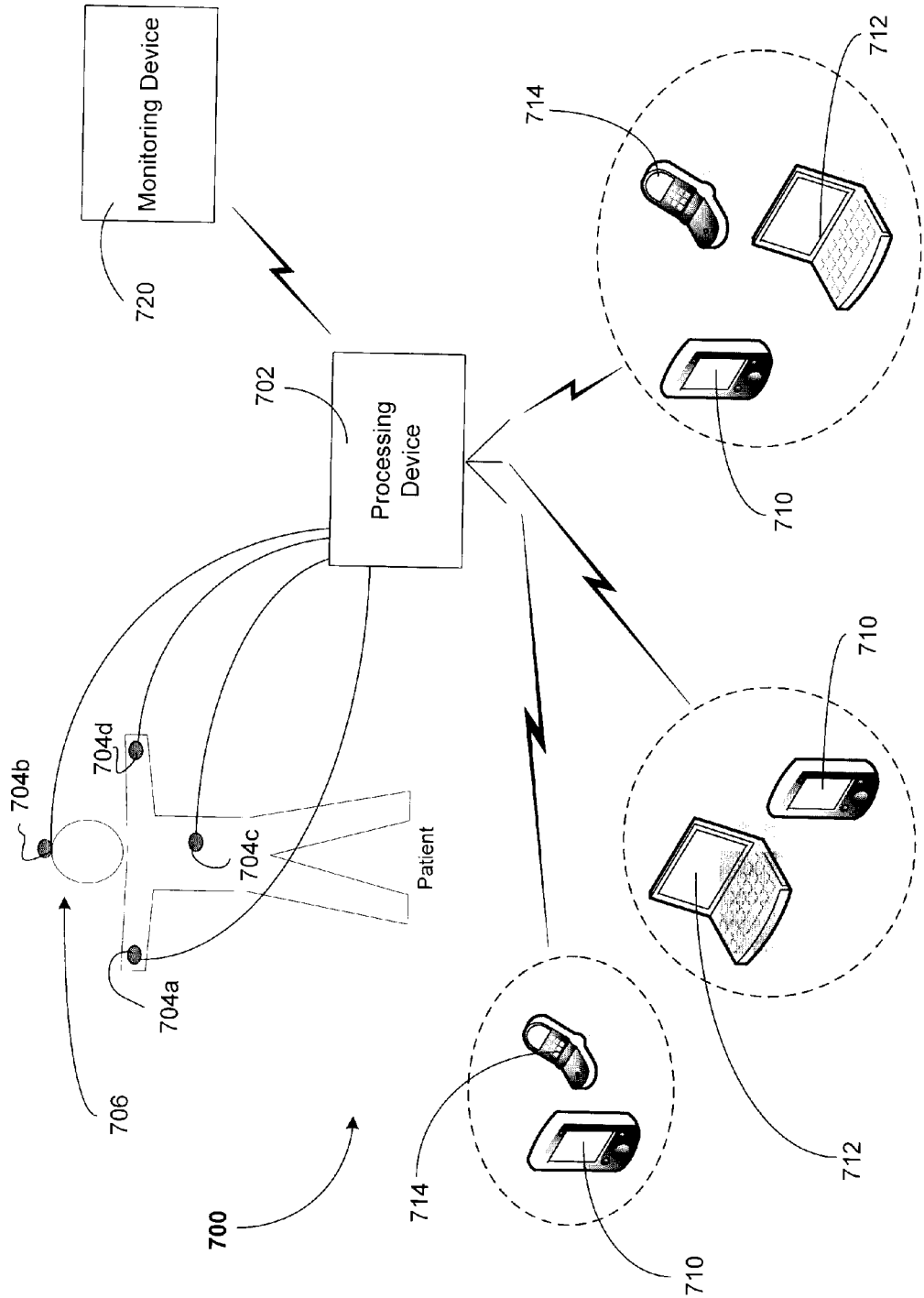
FIG. 8 is a block diagram illustrating an exemplary system implementation associated with the vital sign evaluation tool of FIGS. 1A-3B.

FIG. 7 is a block diagram 700 illustrating an exemplary system associated with the vital sign evaluation tool. As shown, a processing device 702 such as a computer or medical instrument may be communicatively coupled to several vital sign measurement devices 704a-704d. The vital sign measurement devices 704a-704d are coupled to a patient 706 and communicate vital sign measurement data to the processing device 702 either via a wired connection (e.g., shielded cable) or a wireless link (e.g., Infrared, radio frequency (RF), etc.). The processing device 702 is adapted to execute the processing steps described in relation with FIGS. 4 and 5. Upon processing the vital signs and generating a total score, the processing device 702 may transmit a response to medical personnel via several mobile devices such as personal digital assistants (PDAs) 710, cell phones 712, and computers 714. The response may include, but is not limited to, paging medical teams, requesting additional medical resources, and generating other suitable responses by communicating to other monitoring equipment 720, individuals, groups, or teams. The processing device may also generate graphical displays of total score values calculated at designated time intervals for each patient registered with the system 700. Various statistical calculations may also be carried on this data (i.e., total score values) in order to predict and address a patient's condition prior to the occurrence of an adverse event such as death or permanent disability.

Although preferred embodiments of the present invention have been described, those of skill in the art will appreciate that variations and modifications may be made without departing from the spirit and scope thereof as defined by the appended claims.

What is claimed is:

1. A computer implemented method of determining a measure associated with a severity of illness of a patient, the method comprising:

receiving, by the computer, information indicating the age of the patient;

receiving, by the computer, measurement data pertaining to the patient, the measurement data comprising a plurality of vital signs including respiratory rate, heart rate, respiratory effort, oxygen therapy, capillary refill time, transcutaneous oxygen saturation, and systolic blood pressure;

determining, by the computer, for each vital sign a set of ranges, wherein each range has associated therewith a score value based on a severity of illness, and wherein the upper and lower bounds of each range are determined based on the age of the patient;

processing, by the computer, the measurement data to identify, for each vital sign, a corresponding range and a corresponding score value, thereby obtaining a set of score values; and processing, by the computer, the set of score values and calculating a total score associated with a severity of illness of the patient.

2. The method according to claim 1 wherein the score value comprises an integer value that increases based on the vital sign deviating from normality.

3. The method according to claim 1 wherein the total score comprises an integer value that increases based on an increase in the severity of illness.

4. The method according to claim 1 further comprising processing the total score to determine one or more care recommendations.

5. The method according to claim 4 wherein the one or more care recommendations comprise admission of the patient to an intensive care unit (ICU) based on the total score exceeding a pre-determined threshold.

6. The method according to claim 4 wherein the one or more care recommendations comprise the scheduling of a patient assessment.

7. The method according to claim 1 further comprising processing the total score to predict the occurrence of an adverse event.

8. The method according to claim 1 further comprising processing the total score to determine a resource allocation recommendation.

9. The method according to claim 8 further comprising processing a plurality of total scores associated with a plurality of patients to determine a resource allocation recommendation.

10. The method according to claim 9 wherein the resource allocation recommendation comprises a determination of medical staffing needs.

11. The method according to claim 10 wherein the determination of medical staffing needs comprises a determination of a number of nurses.

12. The method according to claim 1 further comprising determining, based on the total score, a designated time interval for subsequent documentation of the set of measurements for the patient.

13. The method according to claim 12 wherein the designated time interval is determined, at least in part, based on whether or not the total score is obtained as an initial determination of the total score or as a subsequent determination of the total score.

14. The method according to claim 12 wherein the designated time interval is determined, at least in part, based on whether or not the total score has deviated from a previous determination of the total score.

15. The method according to claim 1 further comprising calculating the total score at multiple times during a time interval.

16. The method according to claim 15 further comprising processing the total scores obtained at multiple times to determine, based on changes in the total score, a measure of the severity of illness based on changes in the total score.

17. The method according to claim 15 wherein the total score is calculated at pre-determined time intervals.

18. The method according to claim 17 wherein one or more of the pre-determined time intervals are determined based on the total score.

19. The method according to claim 15 further comprising evaluating a variation in score value for at least one vital sign based on score value calculated at pre-determined time intervals.

20. The method according to claim 1 further comprising evaluating a medical condition indication associated with the patient based on the variation in the score value.

21. The method according to claim 1 further comprising displaying the measurement data on a grid.

22. The method according to claim 21 wherein the grid comprises a chronological axis that is adapted to for displaying the score value at one or more times during a time period.

23. The method according to claim 21 wherein the grid comprises a plurality of color-coded sections associated with each vital sign, and wherein each color-coded section has a score value associated therewith.

24. The method according to claim 23 wherein each one of the plurality of color-coded sections comprises at least one color-coded row.

25. The method according to claim 1 wherein the upper and lower bounds of the each range are customized for pediatric patients.

26. The method according to claim 1 wherein one or more vital sign measurement devices are operatively coupled to the patient, and wherein the measurement data is received by a processing device connected to the one or more vital sign measurement devices.

27. The method according to claim 1 further comprising:
generating a response based on the total score; and
transmitting the response to at least one mobile computing device.

28. The method according to claim 27 wherein the at least one mobile computing device includes a mobile communications device.

29. The method according to claim 27 wherein the at least one mobile computing device includes an additional monitoring device.

* * * * *